(12) United States Patent
Levy et al.

(10) Patent No.: US 7,589,070 B2
(45) Date of Patent: Sep. 15, 2009

(54) SURFACE MODIFICATION FOR IMPROVING BIOCOMPATIBILITY

(75) Inventors: Robert J. Levy, Merion Station, PA (US); Ivan Alferiev, Clementon, NJ (US); Cunxian Song, Philadelphia, PA (US); Ilia Fishbein, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 308 days.

(21) Appl. No.: 10/170,411

(22) Filed: Jun. 14, 2002

(65) Prior Publication Data

US 2003/0044408 A1 Mar. 6, 2003

Related U.S. Application Data

(60) Provisional application No. 60/298,116, filed on Jun. 15, 2001.

(51) Int. Cl.
*A61K 31/70* (2006.01)
*A01N 43/04* (2006.01)
*A61K 39/395* (2006.01)
*A61F 2/00* (2006.01)

(52) U.S. Cl. .............. 514/44; 514/6; 514/12; 514/393; 424/130.1; 424/423

(58) Field of Classification Search .............. 424/130.1, 424/93.21; 623/1.15; 604/500; 514/44; 435/320.1
See application file for complete search history.

(56) References Cited

U.S. PATENT DOCUMENTS

| 5,132,181 | A | * | 7/1992 | Wefers et al. | 428/457 |
|---|---|---|---|---|---|
| 5,354,554 | A | * | 10/1994 | Rhind | 424/1.49 |
| 5,439,829 | A | | 8/1995 | Anderson et al. | |
| 6,096,018 | A | * | 8/2000 | Luzio et al. | 604/500 |
| 6,153,598 | A | | 11/2000 | Filler et al. | |
| 6,261,554 | B1 | * | 7/2001 | Valerio et al. | 424/93.6 |
| 2001/0002411 | A1 | * | 5/2001 | Ronan et al. | 523/113 |
| 2003/0004564 | A1 | * | 1/2003 | Elkins et al. | 623/1.15 |
| 2004/0029280 | A1 | * | 2/2004 | Sosnowski et al. | 435/456 |

FOREIGN PATENT DOCUMENTS

| DE | 301459 A7 * | 7/1987 |
|---|---|---|
| EP | 0914835 A2 | 5/1999 |
| WO | WO 97/06195 A1 | 2/1997 |
| WO | WO 99/62079 A1 | 12/1999 |

OTHER PUBLICATIONS

Nishikawa et al. Human Gene Therapy 12:861-870, 2001.*
Romano et al. Stem Cell, 18:19-39, 2000.*
Fry et al. Expert Reviews in molecular Medicine, ISSN 1462-3994, published Jun. 8, 1999, pp. 1-24.*

* cited by examiner

*Primary Examiner*—Janet L Epps-Smith
(74) *Attorney, Agent, or Firm*—RatnerPrestia

(57) ABSTRACT

A therapeutic delivery system efficiently introduces biologically active molecules to mammalian cells without the use of synthetic polymers or biopolymer coatings. Surface modification of a metal support, such as a medical device, results in a single molecular layer that can fasten various molecules, thereby minimizing any cellular inflammatory response while enhancing biocompatibility.

55 Claims, 14 Drawing Sheets

General formula of functionalized bisphosphonate

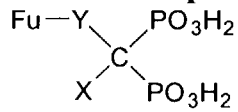

X = H, Alk, OH or other suitable substituent;
Fu = NH$_2$, SH (also, in a latent form), or an alkylating function, like maleimido or vinylsulfonyl group;
Y = aliphatic, arylaliphatic, or aromatic spacer, which can be a polymer, bearing many bisphosphonate and reactive functional groups

Figure 1b

3-Amino-1-hydroxypropylidene-1,1-bisphosphonic (pamidronic) acid

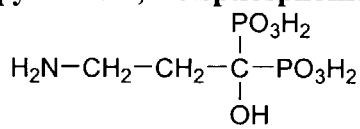

Figure 1c

Polyallylamine modified with 2,2-diphosphonoethyl groups (PAA-BP)

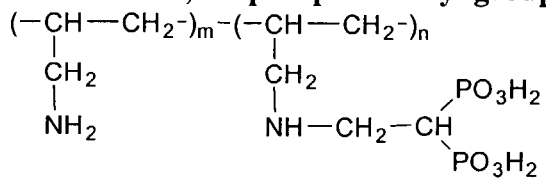

Chemosorption of functionalized bisphosphonates on the metal surface

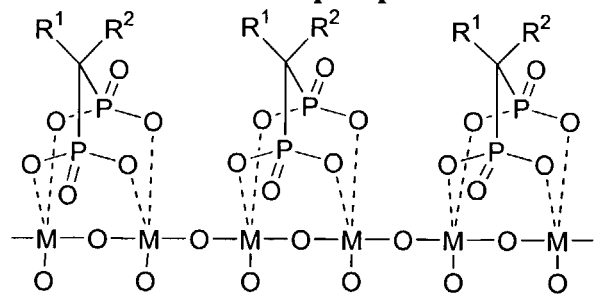

Chemosorption layer of bisphosphonate

M = metal (Fe, Cr, etc.), R$^1$ = H, OH, Alk; R$^2$ = Alk (also, containing functional groups)

Cross-linking antibodies to the metal surface via chemosorbed bisphosphonate containing amino groups.

Cross-linking antibodies to the metal surface via chemosorbed bisphosphonate (monomeric or polymeric) containing latent thiol groups Synthesis of a Polyallylamine Modified with Bisphosphonate Groups (PAA-BP)

m + n = 100 to 1000; n/(m + n) = 0.3 to 0.8

Attachment of antibodies to the metal surface via chemosorbed bisphosphonate (monomeric or polymeric) containing thiol-reactive vinylsulfonyl groups M = metal; X and Y as in the general formula (Y can be either monomeric or polymeric);
Z = aliphatic, arylaliphatic, or aromatic spacer DMSO = dimethyl sulfoxide EDAC = 1-ethyl-3-dimethylaminopropylcarbodiimide m + n = 100 to 1000; n/(m + n) = 0.3 to 0.8; l/(m+n) = 0.1 to 0.3;
DMF = dimethylformamide; Et$_3$N = triethylamine Bio = covalently attached biotin

SURFACE MODIFICATION FOR IMPROVING BIOCOMPATIBILITY

This application claims the benefit of provisional U.S. Application Ser. No. 60/298,116, filed Jun. 15, 2001.

BACKGROUND OF THE INVENTION

The present invention relates to surface modification of metal supports, including medical devices, to specifically and efficiently introduce biologically active molecules and macromolecules into mammalian cells. Of particular interest is a delivery system for nucleic acid without the use of surface coatings, thereby enhancing biocompatibility.

Many types of metal supports, such as stainless steel and titanium medical devices have mechanical properties that are advantageous, but are generally incompatible with blood or tissue. To this end, polymer coatings for metal supports have been developed in the anticipation of improving biocompatibility and minimizing the battery of adverse cellular responses associated with foreign materials.

Surface coatings and treatments, however, are problematic in that they can invoke acute or chronic inflammatory responses due to the coatings themselves. The use of synthetic polymers and biopolymer coatings for delivery purposes can, in some instances, also result in an undesirable hyper-proliferation response among cells that contact the polymeric material. Polyurethane, poly(dimethyl siloxane) and polyethylene terephthalate coated stents cause inflammation and thrombus formation. Low molecular weight poly-L-lactic acid coating also causes an inflammatory response. Lincoff et al., *J. Am. Coll. Cardiol.*, 29, 808.16 (1997). Polymer coated medical devices for drug delivery have also been met with little success.

Nucleic acid delivery from coatings have also been problematic in that the ability to transfer nucleic acid efficiently into a targeted cell population and achieve a high level of expression of the gene product in vivo is limited. Incorporating plasmid DNA into a collagen sponge and implanting it in bone can successfully deliver the nucleic acid, but most of the DNA escapes in a very short time (less than one hour). Bonadio et al., *Nat. Med.* 1999, 5(7):753-9. In principle, therefore, larger amounts of nucleic acid would be required for adequate delivery. Id. Various DNA delivery systems have been employed to localize and sustain gene transfer activity in this context, with mixed results.

SUMMARY OF THE INVENTION

The present invention addresses the need for methodology to deliver a biologically active molecule without the use of polymer coatings. Surface modification of biocompatible metal supports creates a therapeutic delivery system for nucleic acid, protein and pharmaceuticals.

The present invention also addresses the need for compositions that can be used to deliver therapeutic polynucleotides, proteins and pharmaceuticals to an in vivo site and retain such therapeutic agents at that site, while minimizing adverse responses due to polymer coatings.

According with one aspect of the present invention, therefore, is a composition comprising a surface modifier and a metal support to which said surface modifier is chemically coordinated. Preferably, the surface modifier is an aminobisphosphonate. Still preferred, the surface modifier is a polyamine. In another aspect of the invention, the composition further comprises a biologically active molecule. In another preferred embodiment, the biologically active molecule is an antibody which specifically binds a nucleic acid. Also preferred, the nucleic acid comprises a vector system. In yet another aspect of the invention, the biologically active molecule is preferably one component of an affinity pairing system. Still preferred, the biologically active molecule is avidin or biotin; IgG or protein A; or transferrin or its receptor.

Another object of the invention provides a method of making a modified metal support comprising (i) adding a surface modifier to a metal support and (ii) reacting said metal support with a crosslinker. In a preferred embodiment, the surface modifier is an aminobisphosphonate. Preferably, the aminobisphosphonates are polybisphosphonates. Also preferred is a polyamine surface modifier.

In yet another aspect, the present invention provides a method of making a therapeutic delivery system, comprising (i) modifying a metal support and (ii) linking a biologically active molecule to said modified metal support. In one preferred embodiment, the metal support is a medical device, such as a stainless steel stent.

In a related vein, a method for delivering a biologically active molecule, comprising (A) exposing a cell to a complex comprised of (i) a biologically active molecule, (ii) a surface modifier and (iii) a metal support to which said aminobisphonates are chemically coordinated. In a preferred embodiment, the biologically active molecule is an antibody.

BRIEF DESCRIPTION OF DRAWINGS

FIGS. 1a, 1b, 1c, and 1d. FIG. 1a shows the general chemical structure of a monomeric or polymeric functionalized bisphosphonate suitable for the modification of metal surfaces to bind proteins thereon. FIG. 1b shows pamidronic acid as an example of a functionalized monomeric bisphosphonate. FIG. 1c shows polyallylamine modified with bisphosphonate groups (PAA-BP) as an example of a functionalized polymeric bisphosphonate. FIG. 1d shows generally the chemosorption layer of functionalized bisphosphonates on the metal surface.

FIG. 9a depicts the synthesis of 3-propyldithiopropionic acid. FIG. 9b shows the activation of the carboxy group in this acid via N-hydroxysuccinimide esterification. FIG. 9c describes the introduction of 3-propyldithiopropionyl residues into polyaminobisphosphonates derived from polyallylamine. FIG. 9d depicts the use of low molecular weight (LMW) and high molecular weight (HMW) thiol-modified PAABP to compare the densities of fluorescent groups attached to SH-reactive sites on metal surfaces that are untreated or pre-treated with either a mixture of nitric acid and isopropanol, hydrochloric acid and isopropanol, or isopropanol.

FIG. 11a is a graph depicting the quantitation of antibody-binding sites on steel showing the superiority of low molecular weight (LMW) to high molecular weight (HMW) polyallylaminobisphosphonate (PAABP). FIG. 11b is a graph comparing the stabilities of SH-reactive groups linked to PAABP after one week at pH 7.4.

FIG. 12 is a baseline spectrum of a stainless steel rod, showing a high proportion of metal signals (phosphorus percent by weight=0%). FIG. 12 is a spectrum after reaction with pamidronate at pH 7, demonstrating an increase in phosphorus to 1% by weight. FIG. 12 is a spectrum after reaction with pamidronate at pH 5, showing further increases in phosphorus, to 13% by weight, and undetectable metal signals.

DETAILED DESCRIPTION OF PREFERRED EMBODIMENTS

Figure 2:
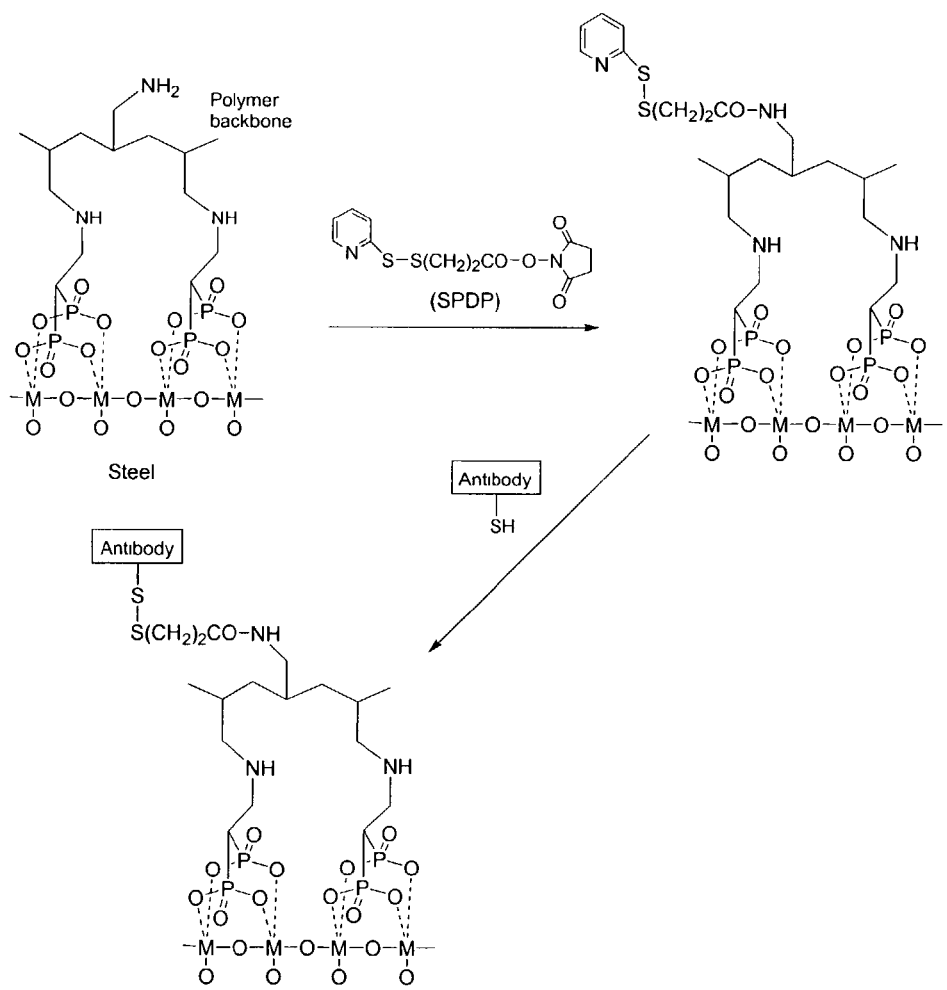
FIG. 2 depicts a reaction scheme for modifying surfaces of metal supports via amino group containing bisphosphonates. During an activation step, the N-succinimidyl ester group in SPDP (N-succinimidyl-3-(2-pyridyldithio)-propionate) reacts with the amino group of a chemosorbed polyaminobisphosphonic acid, to activate a steel surface with a pyridyldithio group. During a modification step, a thiol modified antibody is chemically linked to the metal.

The inventors have discovered a composition for delivering a biologically active molecule without the use of polymers and other dense coatings, thereby minimizing an inflammatory response. Thus, the present invention contemplates a chemical modification of a metal support for attachment of proteins, peptides, and pharmaceuticals. This disclosure advances the field by providing a biocompatible means for introducing, into mammalian cells, biologically active molecules that have therapeutic utility.

Surprisingly, the inventors have found a way to deliver a biologically active molecule via the attachment of one component of an affinity ligand pairing system to a metal surface. The component is able to bind a vector, for example, which is capable of delivering the biologically active molecule. The paired component which is most suitable for attachment to the surface-modified metal would be immobilized. The component is covalently cross-linked to a monomeric or polymeric surface modifier, which, in turn, provides chemical moieties that bind to the metal surface. Thus, the present invention, for example, provides a way to attach a gene delivery system using metal surface modification, comprising linking an anti-nucleic acid antibody to the metal support. Although nucleic acid-binding antibodies were known, their usefulness to the ends of gene delivery was not appreciated heretofore. Yet the inventors have demonstrated that a polynucleotide bound specifically to an antibody, which in turn is "fastened" to a support, embodies an efficient system for cell transfection and transduction.

The metal support of the invention can take the form of any medical device that is suited for, or that is adaptable to, placing the surface-immobilized molecule in the targeted region. For example, the metal support can be an implant, such as a stent, which can then be linked to a protein or pharmaceutical composition. Surface modification of the metal support results in a single molecular layer that can fasten biologically active molecules.

The Biologically Active Molecule

The biologically active molecule of the present invention can be any molecule or macromolecule to which a suitable reactive group, such as a carboxy (—COOH), amino (—NH$_2$) or thiol group (—SH) is attached. For example, proteins or peptides that have been modified to comprise a thiol group or comprise an amino group can be used. The biologically active molecule also has therapeutic utility.

Suitable biologically active molecules include pharmaceuticals, nucleic acid sequences, such as transposons, signaling proteins that facilitate wound healing, such as TGF-β, FGF, PDGF, IGF, and GH proteins that regulate cell survival and apoptosis, such as Bcl-2 family members and caspases; tumor suppressor proteins, such as the retinoblastoma, p53, APC, DCC, NF1, NF2, RET, VHL and WT-1 gene products; extracellular matrix proteins, such as laminins, fibronectins and integrins; cell adhesion molecules such as cadherins, N-CAMs, selectins and immunoglobulins; anti-inflammatory proteins such as Thymosin beta-4, IL-10 and IL-12.

Additionally, the biologically active molecule can be either component of any affinity ligand pair. Examples of such affinity ligand pairs include avidin-biotin and IgG-protein A. Furthermore, the biologically active molecule can be either component of any receptor-ligand pair. One example is transferrin and its receptor. Other affinity ligand pairs include powerful hydrogen bonding or ionic bonding entities such as chemical complexes. Examples of the latter include metallo-amine complexes. Other such attractive complexes include nucleic acid base pairs, via immobilizing oligonucleotides of a specific sequence, especially antisense. Nucleic acid decoys or synthetic analogues can also be used as pairing agents to bind a designed gene vector with attractive sites. Furthermore, DNA binding proteins can also be considered as specific affinity agents; these include such entities as histones, transcription factors, and receptors such as the gluco-corticoid receptor.

In one preferred embodiment, the biologically active molecule is an anti-nucleic acid antibody. The antibody can therefore specifically bind a nucleic acid which encodes a product (or the precursor of a product) that decreases cell proliferation or induces cell death, thereby mitigating the problem of restenosis in arteries and other vessels. The nucleic acid that is tethered to a support via the antibody can efficiently transfect/ transduce cells. In general terms, the field of "gene therapy" involves delivering into target cells some polynucleotide, such as an antisense DNA or RNA, a ribozyme, a viral fragment, or a functionally active gene, that has a therapeutic or prophylactic effect on the cell or the organism containing it. Culver, 1994, GENE THERAPY: A HANDBOOK FOR PHYSICIANS (Mary Ann Liebert, Inc., New York, N.Y.). The antibody of the composition can be a full-length (i.e., naturally occurring or formed by normal immuno-globulin gene fragment recombinatorial processes) immunoglobulin molecule (e.g., an IgG antibody, or IgM or any antibody subtype) or an immunologically active (i.e., specifically binding) portion of an immuno-globulin molecule. The antibody comprises one or more sites which specifically bind with a nucleic acid (i.e., which does not substantially bind other types of molecules). The binding site can be one which binds specifically with a nucleic acid of a desired type without regard to the nucleotide sequence of the nucleic acid. The binding site can, alternatively, be one which binds specifically only with a nucleic acid comprising a desired nucleotide sequence. Preferably, the antibody is a thiol modified antibody.

The complex formed between a polynucleotide and a cognate antibody can be immobilized on a variety of surfaces such that, when the surface is exposed to a physiological environment in situ, the attached polynucleotide is released, over time, in a manner that enhances delivery of the polynucleotide to cells in the proximity. Surprisingly, DNA transfer by way of immunospecific tethering maintains the nucleic acid in regions that are subject to gene therapy.

Examples of suitable antibodies include Fv, F(ab), and F(ab')$_2$ fragments, which can be generated is conventional fashion, as by treating an antibody with pepsin or another proteolytic enzyme. The nucleic acid-binding antibody used in a composition of the present invention can be a polyclonal antibody or a monoclonal antibody. A "monoclonal" antibody comprises only one type of antigen binding site that specifically binds with the nucleic acid. A "polyclonal" antibody can comprise multiple antigen binding sites that specifically bind the nucleic acid. An antibody employed in this invention preferably is a full-length antibody or a fragment of an antibody, such as F(ab')$_2$, that possesses the desired binding properties.

The Metal Support

In this description, "metal support" denotes a uniform, solid homogenous or heterogenous material support, or a network of supporting structures suitable for gene therapy in accordance with the present invention. The metal support can be any structure having a metal surface, including medical devices. A "medical device" is any tool, mechanism, or apparatus that can be used during medical intervention, including but not limited to surgical implants, surgical sutures, and prostheses.

Illustrative of suitable metallic materials are stainless steel, MP35 stainless steel, aluminum oxide, platinum, platinum alloys, elgiloy, tivanium, vitallium, titanium, titanium alloys, Nitinol (nickel-titanium alloy), chromium alloys and cobalt based alloys and the like. Oxides of these metals and alloys can also be used. In a preferred embodiment, a medical device with a stainless steel surface, such as a stent, is also preferred. The metallic surface can be modified to facilitate attachment of the biologically active molecule without the use of polymers and other coatings.

Medical devices appropriate for the gene delivery system in the present invention include, but are not limited to, heart valves, wire sutures, temporary joint replacements and urinary dilators. Other suitable medical devices for this invention include orthopedic implants such as joint prostheses, screws, nails, nuts, bolts, plates, rods, pins, wires, inserters, osteoports, halo systems and other orthopedic devices used for stabilization or fixation of spinal and long bone fractures or disarticulations. Other devices may include non-orthopedic devices, temporary placements and permanent implants, such as tracheostomy devices, intraurethral and other genitourinary implants, stylets, dilators, stents, vascular clips and filters, pacemakers, wire guides and access ports of subcutaneously implanted vascular catheters.

The Surface Modifier

A surface modifier suitable for the present invention is any compound that (i) can chemically coordinate with a metal surface and (ii) has a derivatizable functionality. Examples of such surface modifiers include but are not limited to polybisphosphonates, aminobisphosphonates and polyamines. Aminobisphosphonates include polyaminobisphosphonates. Other surface coordinating compounds with side functionalities, for branching attachment and amplification, include any polymeric, oligomeric, or monomeric compound that contains groups capable of coordination to metal ions, such as phosphonic groups, hydroxamic groups, carboxylic groups, sulfonic residues, sulfinic groups and amino groups. The side functionalities capable of further reactions (when the modifier is already absorbed on the metal surface) could include amino or thiol groups (also in latent modifications, e.g., alkyldithio groups, which can be reduced to thiol groups immediately before the use), alkylating groups (maleimido, vinylsulfonyl, epoxy or iodoacetamido groups), and other groups suitable for the covalent attachment of proteins and at the same time, comparatively inert towards the coordination with the metal ions on the surface.

The polymeric backbone of the polymeric surface modifiers should be sufficiently stable in the aqueous surrounding, and can be represented by a chain consisting purely of carbon atoms (as for the polymers based on polyallylamine), or could incorporate heteroatoms (oxygen nitrogen, etc.) into the polymeric chain (e.g., polylysine, also with a part of lysine residues modified to insert chelating groups for better coordination to the metal). The polymeric surface modifier can be derived from a polyamine or other polymers. For example, it could be a polymer with pendant phosphonate or geminal bisphosphonate groups (for coordination with the metal ions on the surface) and alkyldithio groups as latent thiol functions for the subsequent protein tethering.

A chelating group is a chemical entity consisting of several units capable of coordination to the metal ions and positioned in close proximity to each other, so they could simultaneously bind the same metal ion, thus increasing the strength of the interaction. Chelating groups could contain units capable of formation only metal-oxygen coordination bonds with the metal ions (geminal bisphosphonate, geminal or vicinal dicarboxylate, or hydroxamate), or they also could involve other atoms (e.g., iminodiacetate group, which in addition to the metal-oxygen bonds can also form metal-nitrogen bonds involving the tertiary amino group).

Coordination to the metal surface usually depends on pH and is suppressed in both strongly acidic and strongly alkaline media. Stronger chelators (like geminal bisphosphonate groups) could be used in wide regions of pH (approximately, from 2 to 12), whereas amino groups are much weaker towards the coordination with the metal surface, and probably, would be effective only in a narrow region of pH close to the value of $pK_a$ characteristic to them (ca. 10 for the aliphatic amino groups). All of these, alone or in combinations, would be suitable for coordination chemistry-based surface modifications. Preferably, the surface modifier is an aminobisphosphonate or a polyamine, such as polylysine or polyallylamine. FIG. 1a shows the general formula of bisphosphonates; FIGS. 1b and 1c embody preferred bisphosphonates; and FIG. 1d shows how such bisphosphonates coordinate to a metal surface.

The number of gene vector binding sites can be amplified significantly by repeatedly adding the surface modifier and a crosslinker. A metal surface modified in this manner thus provides a greater potential for immobilization of biologically active molecules. For example, the number of antibody binding sites can be enhanced to ultimately provide greater potential for nucleic acid attachment. In a preferred embodiment, polyamines are reacted with the initial bisphosphonate coordination layer, a crosslinking agent then is added to the polyamines, and the polyamine and crosslinking steps are repeated to attain the desired level of antibody-vector tethering.

For example, the metal surface can be treated with either polyallylaminobisphosphonate (PAABP) or poly-bisphosphonates containing latent thiol groups to form a chemosorption layer with binding through coordination of the bisphosphonate groups. As shown in the reaction sequence in FIG. 2, the primary amino groups of the PAA-BP chemosorption layer can be transformed with SPDP into the thiol-reactive pyridyldithio groups, which then can be used for the immobilization of thiol-containing proteins.

The chemosorption layers of poly-bisphosphonates with latent thiol groups can be reduced with tris(2-carboxyethyl)phosphine (TCEP) in aqueous buffered solutions, at pH ca. 5, for several minutes at room temperature. The immobilized thiol groups thus formed can be then reacted with thiol-reactive groups such as pyridyldithio or maleimido which have been pre-introduced into proteins by standard methods known in the art.

It is also possible to amplify the number of reactive functionalities attached to the chemosorption layer by using several variants of expansion chemistry. One such variant is the reaction of thiol groups on the chemosorption layer with a polymer containing multiple thiol-reactive groups, such as pyridyldithio groups as described above.

Figure 3:
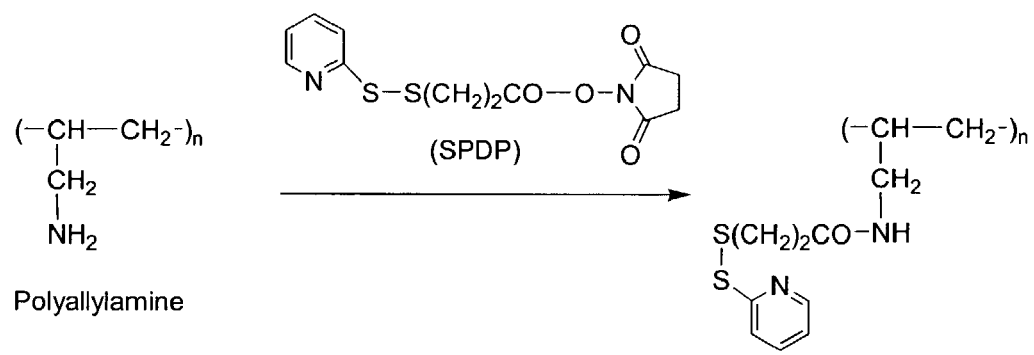
FIG. 3 shows a general reaction by which a latent thiol group can be introduced into a polyallyamine by reaction with SPDP.

For example, pyridyldithio groups rapidly react with thiols in both aqueous (pH 5 to 8) and non-aqueous media, forming stable disulfide linkages. By using a large excess of the PAA-pyridyldithio polymers, most of pyridyldithio groups of the amplification polymer will remain unreacted, and can be later used for the immobilization of thiol-containing proteins. The polymers with multiple pyridyldithio groups are prepared from reactions of SPDP with polymeric amines such as polyallylamine and polyethyleneimine. These polyamines, in their "free base" form, can easily dissolve in non-aqueous solvents (dichloromethane or a mixture of dichloromethane and isopropanol) and smoothly react with SPDP at 0-20° C. (see FIG. 3). The reactions are typically complete in less than 30 min., and no side-reactions (hydrolysis of succinimidyl ester, or degradation of pyridyldithio group) occur. Modified polymers prepared in this manner can be purified from non-polymeric impurities (N-hydroxysuccinimide, and sometimes, an excess of SPDP) by extraction with suitable solvents (methanol or isopropanol).

Using sub-stoichiometrical amounts of SPDP followed by the neutralization of unreacted amino groups with a suitable acid (e. g., HCl), it is also possible to react only a fraction of the amino groups with SPDP, thus obtaining positively charged water-soluble polymers with pyridyldithio groups.

Figure 4:
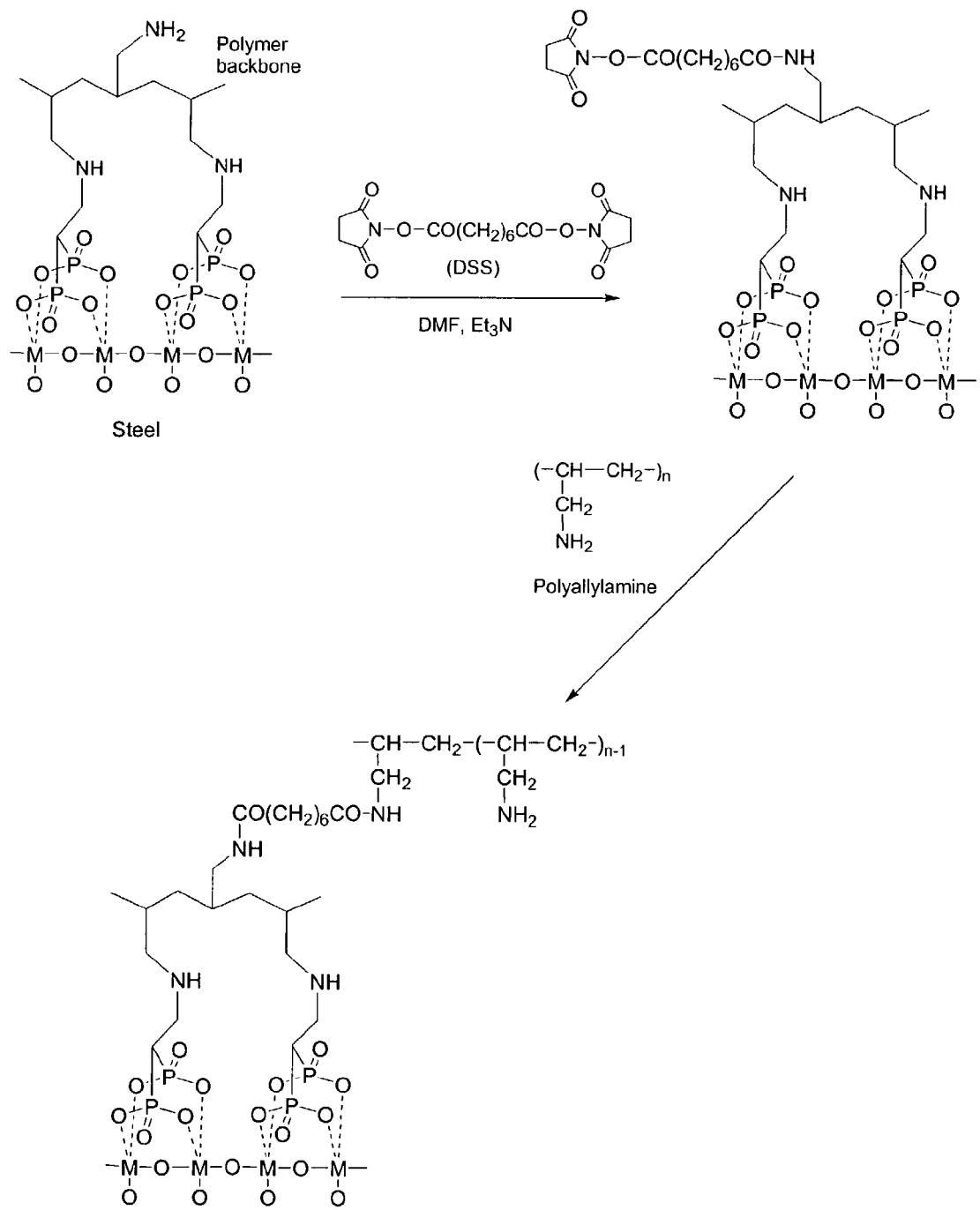
FIG. 4 exemplifies a reaction sequence showing amplification, which employs disuccinimidyl suberate (DSS) as a cross-linker to multiply the number of reactive groups on a metal surface.

Another variant in multiplying the number of reactive groups on the metal surface involves the reaction of PAABP on the metal surface with a suitable homobifunctional (or polyfunctional) amino-reactive cross-linker in a non-aqueous medium followed by treatment with polyallylamine. To eliminate the possibility of hydrolysis, the cross-linker and the amplifier—polyamine should preferably be used in non-aqueous media (e.g., DMF). An organic base (like triethylamine) can be added as the activator of amino groups in the first step, whereas the reaction between immobilized succinimidyl ester groups with the polyamine-base does not require any such activation. Under these conditions, the aminolysis of succinimidyl ester groups is usually complete in a few minutes at room temperature. One example of such an amplification employing disuccinimidyl suberate (DSS) as a cross-linker is shown in FIG. 4.

The Nucleic Acid

A nucleic acid for use in the present invention can be any polynucleotide that one desires to transport to the interior of a cell. In this context, a "therapeutic polynucleotide" is a polymer of nucleotides that, when provided to or expressed in a cell, alleviates, inhibits, or prevents a disease or adverse condition, such as inflammation) and/or promotes tissue healing and repair (e.g., wound healing). The nucleic acid can be composed of deoxyribonucleosides or ribonucleosides, and can have phosphodiester linkages or modifed linkages, such as those described below. The phrase "nucleic acid" also encompasses polynucleotides composed of bases other than the five that are typical of biological systems: adenine, guanine, thymine, cytosine, and uracil.

A suitable nucleic acid can be DNA or RNA, linear or circular and can be single- or double-stranded. The "DNA" category in this regard includes: cDNA; genomic DNA; triple helical, supercoiled, Z-DNA, and other unusual forms of DNA; polynucleotide analogs; an expression construct that comprises a DNA segment coding for a protein, including a therapeutic protein; so-called "antisense" constructs that, upon transcription, yield a ribozyme or an antisense RNA; viral genome fragments, such as viral DNA; plasmids and cosmids; and a gene or gene fragment.

The nucleic acid also can be RNA, for example, antisense RNA, catalytic RNA, catalytic RNA/protein complex (i.e., a "ribozyme"), an expression construct comprised of RNA that can be translated directly, generating a protein, or that can be reverse transcribed and either transcribed or transcribed and then translated, generating an RNA or protein product, respectively; transcribable constructs comprising RNA that embodies the promoter/regulatory sequence(s) necessary for the generation of DNA by reverse transcription; viral RNA; and RNA that codes for a therapeutic protein, inter alia. A suitable nucleic acid can be selected on the basis of a known, anticipated, or expected biological activity that the nucleic acid will exhibit upon delivery to the interior of a target cell or its nucleus.

The length of the nucleic acid is not critical to the invention. Any number of base pairs up to the full-length gene may be transfected. For example, the nucleic acid can be a linear or circular double-stranded DNA molecule having a length from about 100 to 10,000 base pairs in length, although both longer and shorter nucleic acids can be used.

The nucleic acid can be a therapeutic agent, such as an antisense DNA molecule that inhibits mRNA translation. Alternatively, the nucleic acid can encode a therapeutic agent, such as a transcription or translation product which, when expressed by a target cell to which the nucleic acid-containing composition is delivered, has a therapeutic effect on the cell or on a host organism that includes the cell. Examples of therapeutic transcription products include proteins (e.g., antibodies, enzymes, receptor-binding ligands, wound-healing proteins, anti-restenotic proteins, anti-oncogenic proteins, and transcriptional or translational regulatory proteins), anti-sense RNA molecules, ribozymes, viral genome fragments, and the like. The nucleic acid likewise can encode a product that functions as a marker for cells that have been transformed, using the composition. Illustrative markers include proteins that have identifiable spectroscopic properties, such as green fluorescent protein (GFP) and proteins that are expressed on cell surfaces (i.e., can be detected by contacting the target cell with an agent which specifically binds the protein).

A nucleic-acid category that is important to the present invention encompasses polynucleotides that encode proteins that affect wound-healing. For example, the genes egf, tgf, kgf, hb-egf, pdgf, igf, fgf-1, fgf-2, vegf, other growth factors and their receptors, play a considerable role in wound repair.

Another category of polynucleotides, coding for factors that modulate or counteract inflammatory processes, also is significant for the present invention. Also relevant are genes that encode an anti-inflammatory agent such as MSH, a cytokine such as IL-10), or a receptor antagonist that diminishes the inflammatory response.

Suitable polynucleotides can code for an expression product that induces cell death or, alternatively, promotes cell survival, depending on the nucleic acid. These polynucleotides are useful not only for treating tumorigenic and other abnormal cells but also for inducing apoptosis in normal cells. Accordingly, another notable nucleic-acid category for the present invention relates to polynucleotides that, upon expression, encode an anti-oncogenic protein or, upon transcription, yield an anti-oncogenic antisense oligonucleotide. (In this context, the phrases "anti-oncogenic protein" and "anti-oncogenic antisense oligonucleotide" respectively denote a protein or an antisense oligonucleotide that, when provided to any region where cell death is desired, or the site of a cancerous or pre-cancerous lesion in a subject, prevents, inhibits, or reverses abnormal and normal cellular growth at the site or induces apoptosis of cells.) Delivery of such a polynucleotide to cells, pursuant to the present invention, can inhibit cellular growth, differentiation, or migration to prevent movement or unwanted expansion of tissue at or near the site of transfer. Illustrative of this anti-oncogenic category are polynucleotides that code for one of the known anti-oncogenic proteins. Such a polynucleotide would include, for example, a nucleotide sequence taken or derived from one or more of the following genes: abl, akt2, apc, bcl2-alpha, bcl2-beta, bcl3, bcl-x, bad, bcr, brca1, brca2, cb1, ccnd1, cdk4, crk-II, csflr/fms, dbl, dcc, dpc4/smad4, e-cad, e2fl/rbap, egfr/erbb-l, elk1, elk3, eph, erg, ets1, ets2, fer, fgr/src2, flil/ergb2, fos, fps/fes, fral, fra2, fyn, hck, hek, her2/erbb-2/neu, her3/erbb-3, her4/erbb-4, hras1, hst2, hstfl, ink4a, ink4b, int2/fgf3, jun, junb, jund, kip2, kit, kras2a, kras2b, ck, lyn, mas, max, mcc, met, mlh1, mos, msh2, msh3, msh6, myb, myba, mybb, myc, mycl1, mycn, nf1, nf2, nras, p53, pdgfb, pim1, pms1, pms2, ptc, pten, raft, rb1, rel, ret, ros1, ski, src1, tal1, tgfbr2, thra1, thrb, tiam1, trk, vav, vhl, waf1, wnt1, wnt2, wt1, and yes1. By the same token, oligonucleotides that inhibit expression of one of these genes can be used as anti-oncogenic antisense oligonucleotides.

Nucleic acids having modified internucleoside linkages also can be used in a composition according to the present invention. For example, nucleic acids can be employed that contain modified internucleoside linkages which exhibit increased nuclease stability. Such polynuclotides include, for example, those that contain one or more phosphonate, phosphorothioate, phosphorodithioate, phosphoramidate methoxyethyl phosphoramidate, formacetal, thioformacetal, diisopropylsilyl, acetamidate, carbamate, dimethylene-sulfide ($-CH_2-S-CH_2-$), dimethylene-sulfoxide ($-CH_2-SO-CH_2-$), dimethylene-sulfone ($-CH_2-SO_2-CH_2-$), 2'-O-alkyl, and 2'-deoxy-2'-fluoro-phosphorothioate internucleoside linkages.

For present purposes, a nucleic acid can be prepared or isolated by any conventional means typically used to prepare or isolate nucleic acids. For example, DNA and RNA can be chemically synthesized using commercially available reagents and synthesizers by known methods. For example, see Gait, 1985, in: OLIGONUCLEOTIDE SYNTHESIS: A PRACTICAL APPROACH (IRL Press, Oxford, England). RNA molecules also can be produced in high yield via in vitro transcription techniques, using plasmids such as SP65, available from Promega Corporation (Madison, Wis.). The nucleic acid can be purified by any suitable means, and many such means are known. For example, the nucleic acid can be purified by reverse-phase or ion exchange HPLC, size exclusion chromatography, or gel electrophoresis. Of course, the skilled artisan will recognize that the method of purification will depend in part on the size of the DNA to be purified. The nucleic acid also can be prepared via any of the innumerable recombinant techniques that are known or that are developed hereafter.

A suitable nucleic acid can be engineered into a variety of known host vector systems that provide for replication of the nucleic acid on a scale suitable for the preparation of an inventive composition. Vector systems can be viral or non-viral. Particular examples of viral vector systems include adenovirus, retrovirus, adeno-associated virus and herpes simplex virus. Preferably, an adenovirus vector is used. A non-viral vector system includes a plasmid, a circular, double-stranded DNA molecule. Viral and nonviral vector systems can be designed, using known methods, to contain the elements necessary for directing transcription, translation, or both, of the nucleic acid in a cell to which it is delivered. Methods which are known to the skilled artisan can be used to construct expression constructs having the protein coding sequence operably linked with appropriate transcriptional/translational control signals. These methods include in vitro recombinant DNA techniques and synthetic techniques. For in stance, see Sambrook et al., 1989, MOLECULAR CLONING: A LABORATORY MANUAL (Cold Spring Harbor Laboratory, New York), and Ausubel et al., 1997, CURRENT PROTOCOLS IN MOLECULAR BIOLOGY (John Wiley & Sons, New York).

A nucleic acid encoding one or more proteins of interest can be operatively associated with a variety of different promoter/regulator sequences. The promoter/regulator sequences can include a constitutive or inducible promoter, and can be used under the appropriate conditions to direct high level or regulated expression of the gene of interest. Particular examples of promoter/regulatory regions that can be used include the cytomegalovirus (CMV) promoter/regulatory region and the promoter/regulatory regions associated with the SV40 early genes or the SV40 late genes. Preferably, the human CMV promoter is used, but substantially any promoter/regulatory region which directs high level or regulated expression of the gene of interest can be used.

It also is within the scope of the present invention that the employed nucleic acid contains a plurality of protein-coding regions, combined on a single genetic construct under control of one or more promoters. The two or more protein-coding regions can be under the transcriptional control of a single promoter, and the transcript of the nucleic acid can comprise one or more internal ribosome entry sites interposed between the protein-coding regions. Thus, a myriad of different genes and genetic constructs can be utilized.

Method of making a modified metal support

The present invention describes a composition comprising a biologically active molecule and a metal support to which functionalized bisphosphonates are covalently linked. Another aspect of the present invention is a method for making a modified metal support comprising (i) adding a surface modifier to a metal support and (ii) reacting said surface modifier with a crosslinker. Preferably, the surface modifier is an aminobisphosphonate. The general formula of such bisphosphonates, examples of their possible structure and their coordination to the metal surface are depicted in FIGS. 1a-d. The coordination of functionalized bisphosphonates provides a high affinity method of directly loading proteins with suitable reactive groups, like thiol, carboxy, or amino functions, such as antibodies via cross linkers, to a metal support. By virtue of the chelating bisphosphonate groups, the amino bisphosphonate molecules coordinate nearly irreversibly to various metal ions, such as those of iron, chromium and nickel.

A preferred embodiment of the method contemplates the use of a polyamine surface modifier. Polyamines can chemically coordinate with a metal surface and tightly bind steel, for example, in the same manner as aminobisphosphonates. The amino groups of the polyamines that do not coordinate with the metal surface can be derivatized.

Another preferred embodiment of the method employs a polybisphosphonate that comprises multiple bisphosphonate residues and multiple reactive functional groups. Increasing the number of bisphosphonate groups enhances binding affinity to the metal support. Consequently, a greater number of functionalities can be used for the immobilization of proteins, and thus provide greater potential for nucleic acid attachment. Preferably, the aminobisphosphonate is a polybisphosphonate.

Figure 5:
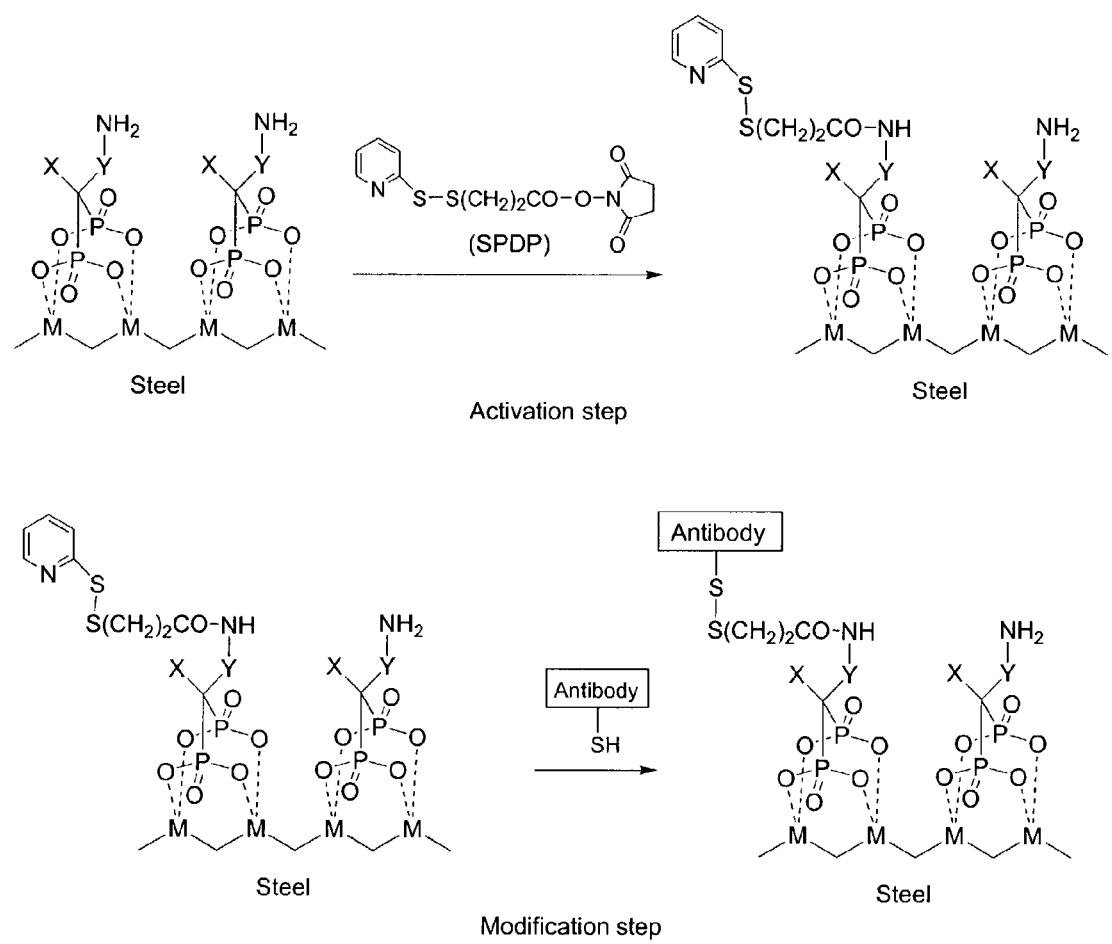
FIG. 5 shows a general reaction sequence by which the crosslinker SPDP (N-succinimidyl-3-(2-pyridyldithio)-propionate) reacts with amino groups of a chemosorbed aminobisphosphonic acid to activate a steel surface with a pyridyldithio group. A thiol-modified antibody can then chemically link to the metal.
Figure 6:
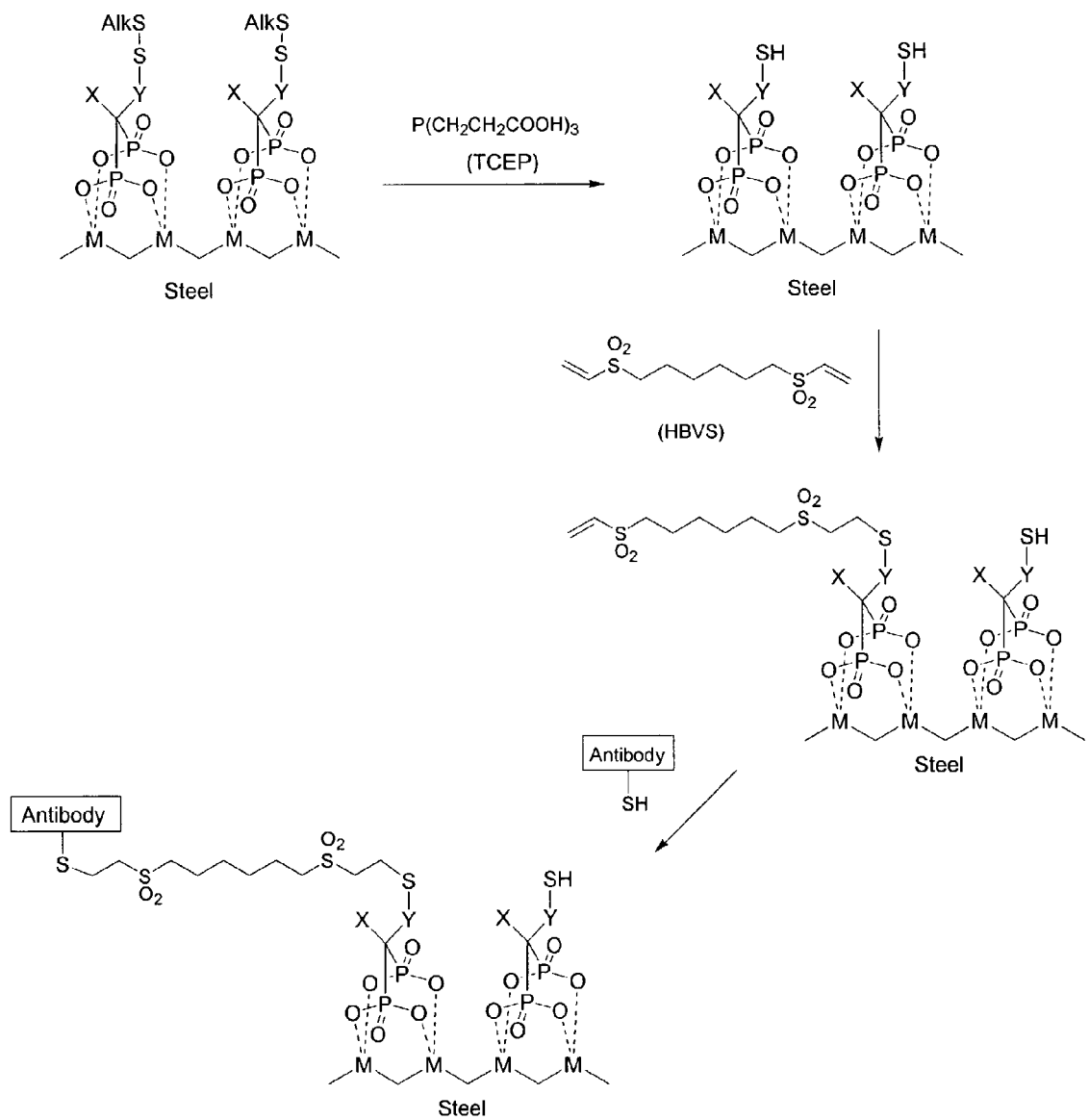
FIG. 6 is a synthetic scheme showing how a metal surface can be modified with bisphosphonates that contain latent thiol groups. The chemosorbed bisphosphonate containing alkyldithio groups are reduced with tris-(carboxyethyl) phosphine (TCEP), to form pendant thiol groups. The latter then are used for linking antibodies via a thiol-to-thiol crosslinker, 1,6-hexane-bis-vinylsulfone (HBVS).

For example, pamidronic acid (3-amino-hydroxypropylidene-1,1-bisphosphonic acid), an amino-bisphosphonic acid, was converted into its potassium salt, in distilled water, to increase the solubility. This pamidronate solution was reacted with the metallic surface, thereby forming coordination bonds between the bisphosphonate groups and the metal cationic sites. In this way, the amino groups were introduced onto the metallic surface, where they could be used as functional groups for further chemical binding. Preferably, the metal support is a stainless steel surface. A heterobifunctional crosslinker such as SPDP (N-succinimidyl-3-(2-pyridyldithio)-propionate) can be employed to link the chemosorbed layer to an antibody, as depicted generally in FIG. 5. However, any crosslinker able to react both with the active functional groups of the chemosorption layer and those of an antibody can be used. Examples of suitable crosslinkers include SPDP, HBVS (1,6-hexane-bis-vinylsulfone, see FIG. 6), EMCS (N-[ε-maleimidocaproyloxy]succinimide ester), BMH (bis-maleimidohexane), DPDPB (1,4-di-[3-(2-pyridyldithio)-propionamido]butane, and other thiol-to-thiol crosslinkers can be used to provide the chemosorption layer with thiol groups.

The SPDP crosslinker reacts with the amine group of bisphosphonate-modified polyallylamine (PAA-BP), chemically linking the pyridyldithio groups of SPDP to the metallic surface. This residue then reacts with a biologically active molecule, which covalently links the molecule to a metal support. In one preferred embodiment of the invention, the biologically active molecule is an antibody. Still more preferred, the antibody is a thiol modified antibody. Such a thiol modified molecule is a substance that comprises a thiol group or has been modified to comprise a thiol group, such as thiol modified protein and peptide.

Figure 7:
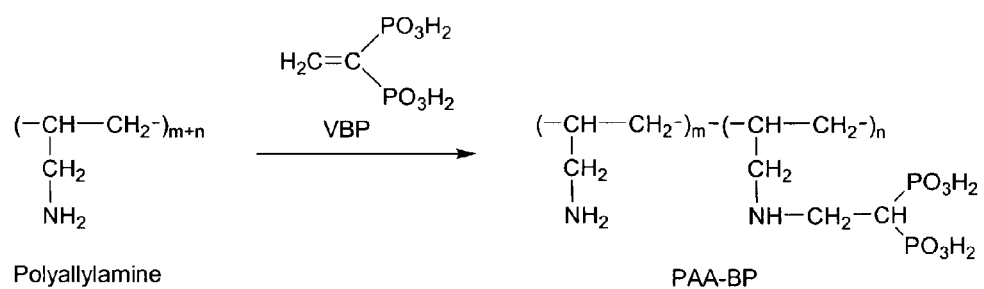
FIG. 7 depicts a reaction scheme for the synthesis of a polyaminobisphosphonate. The Michael addition of primary amino groups of polyallylamine to the activated double bond of vinylidene-bisphosphonic acid (VBP) results in the attachment of 2,2-diphosphonoethyl groups to the polymer. Some amino groups remain unchanged, and therefore can be further used for linking antibodies.

A bisphosphonate-modified polyallylamine (PAA-BP) can be prepared by the nucleophilic addition of the polyallylamine amino groups to the activated double bond of vinylidene-bisphosphonic acid (VBP), as is shown in FIG. 7.

Figure 8:
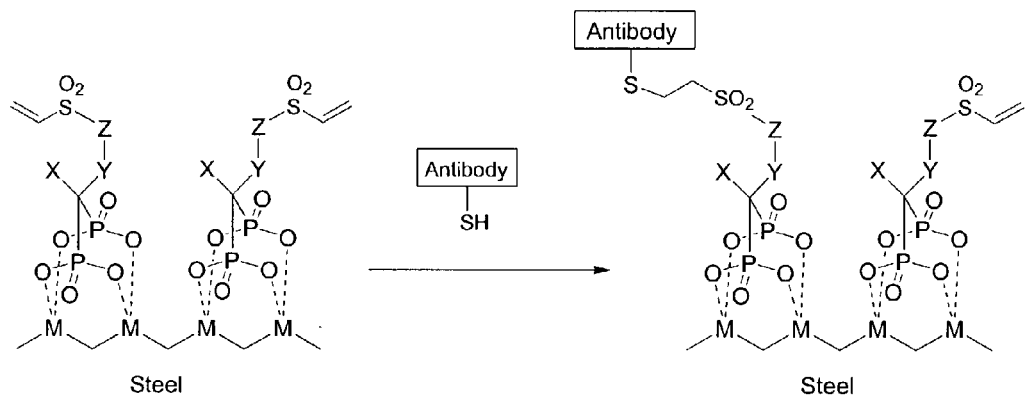
FIG. 8 shows a reaction by which antibodies are cross-linked to the metal surface via the chemosorbed layer of a bisphosphonate (monomeric or polymeric). The bisphosphonate contains a pre-inserted thiol-reactive vinylsulfonyl group.

An additional variant of linking proteins to the metal surface contemplates the use of monomeric or polymeric bisphosphonates already containing reactive groups. Examples of these reactive groups are vinylsulfonyl and maleimido groups, which are inert toward bisphosphonate groups, but reactive toward suitable groups on a protein such as thiol groups. FIG. 8 shows how vinylsulfonyl groups can be employed in this variant.

Method of making a therapeutic delivery system

The present invention also comprehends making a therapeutic delivery system by (i) modifying a metal support and (ii) linking a biologically active molecule to said metal support. The metal surface support is modified as discussed above. Preferably, the aminobisphosphonates are used as the surface modifier. Still preferred, polyamines are used. Also preferred, both aminobisphosphonates and polyamines can be used together to modify the surface of a metal support. In another preferred embodiment, the biologically active molecule is an antibody specific for nucleic acid. Preferably, the antibody is a thiol modified antibody. The immobilized antibody-nucleic acid complex is preferably formed as follows. First, the antibody is linked to a modified metal support. The nucleic acid is then incubated with the immobilized antibody, and the surface is rinsed to remove unbound material, according to conventional methodology. The resultant composition can used in vivo or ex vivo, to transfer nucleic acid to areas targeted for gene therapy. Alternatively, the composition may be used in vitro, in experimental settings, to replace traditional cell transfection/transduction techniques.

Method of delivering a biologically active molecule

Another embodiment of the invention is a method for delivering a biologically active molecule to the cell, comprising (A) exposing a cell to a complex comprised of (i) a biologically active molecule, (ii) a surface modifier and (iii) a metal support to which said surface modifier is chemically coordinated. Preferably, the biologically active molecule is an antibody specifically bound to a nucleic acid and said antibody is bound to said metal support. Still more preferred, the antibody is a thiol modified antibody. The composition can then be used to deliver a nucleic acid to the interior of a cell in need of gene therapy. Antibodies specific for non-viral vectors or nucleic acid may require use of a transfection agent to enhance administration of nucleic acid.

The transfection agent is a cationic macromolecule that is positively charged, comprises two or more art-recognized modular units (e.g., amino acid residues, fatty acid moieties, or polymer repeating units), and is preferably capable of forming supermolecular structures (e.g., aggregates, liposomes, or micelles) at high concentration in aqueous solution or suspension. Among the types of cationic macromolecules that can be used are cationic lipid and polycationic polypeptides.

The amount of the transfection agent to be used when transfecting cells can be calculated based on nucleic acid content of the composition. The capacity of the medium comprising or containing the transfection agent can also affect the amount of transfection agent to be used. When the antibody of the transfection agent is immobilized on a matrix, the amount of cationic macromolecule and DNA that can be complexed with the antibody can be limited by the physical requirements of the metal support. For example, rigidity, flexibility and chemical reactivity may influence the amount of transfection agent used.

If viral vectors are tethered to the metal support, addition of a cationic macromolecule is not necessary for efficient nucleic acid delivery. Viral vectors have been regarded as the most efficient system, and recombinant replication-defective viral vectors have been used to transduce cells both in vitro, in vivo and ex vivo. Such vectors have included retroviral, adenovirus, adeno-associated viral vectors and herpes viral vectors. Cells can be infected with viral vectors by known methods.

The invention is further described with reference to the following examples. These are provided for the purpose of illustration only. Thus, the invention is not limited to these examples, but instead includes all variations that are evident as a result of the teaching provided therein.

EXAMPLE 1a

Synthesis of Polyaminobisphosphonate

Polyallylamine hydrochloride (Sigma-Aldrich, average M=15,000, corresponding to the value of (m+n)=160, 2.22 g, ca. 24 mmol of amino groups) was dissolved in 150 ml water, passed through a column filled with strongly basic anionite Dowex G-55 (OH form, 50 ml of wet resin) and eluted with water until neutral. 300 ml of eluate containing polyallylamine free base was concentrated in vacuo at 40-50° C. to a small volume (ca. 15 ml) and mixed with a solution of vinylidene-bisphosphonic acid hydrate (M~200, 2.36 g. ca 12 mmol) in water (ca. 10 ml). The reaction scheme is shown in FIG. 7. Not paying attention to the formed resinous precipitate, the mixture was dried in vacuo at 60-70 C., 15 mmHg to a transparent glass-like mass (4.74 g), which was then heated at 105-114 C. for 8 hours. After cooling, 100 ml water and 4.2 ml, 30 mmol triethylamine was added. The mixture stirred for 2 days, until complete dissolution of the polymer.

The resultant solution was analyzed using $^{31}$P NMR, which found 92% of bisphosphonate moieties to be bound to the polymer as 2,2 diphosphonoethyl groups with the chemical shift ($\delta$=16.1 ppm) significantly different from this of the starting vinylidene-bisphosphonate ($\delta$=11.5 ppm). As calculated from these data, the modification extent of the modified polyallyamine [100%·n/(m+n)] was 46%. Using this procedure, from about 30% to about 80% of the allylamine groups can be modified by bisphosphonate groups. For changing the extent of the modification, different ratios of reactants can be used with $^{31}$P NMR-monitoring of the reaction. PAABP with different levels of bisphosphonate modifications can be used to determine the optimum conditions for the polymers' chemosorption on the metal surface, and activation of the unblocked amino groups towards the subsequent protein attachment.

Continuing, the solution of polymer (in the form of triethylammonium salt, having pH ~10) was filtered, and the filtrate (diluted with water to 145 ml) was concentrated in vacuo (40-50 C.) to 128 g. Concentrated 36% hydrochloric acid (15 ml, ca. 180 mmol) was added followed by methanol (250 ml). The initially formed resinous precipitate of polymer gradually transformed into a solid powder. The mixture was allowed to stand at ambient temperature for 3 h with periodical rubbing, the precipitate was filtered off, thoroughly washed with methanol (100 ml) and dried overnight in the flow of air at slightly diminished pressure to give 3.95 g of polymer as a white powder. The polymer is almost insoluble in water in acidic conditions (pH from 0 to ca. 6) but dissolves by addition of potassium bicarbonate (ca twofold amount to the weight of the polymer) as the pH is shifting to the slightly alkaline region (7-8).

Analogously, from polyallylamine hydrochloride (Sigma-Aldrich, average M=70,000, corresponding to the value of (m+n)=745, 2.22 g, ca. 24 mmol of amino groups) and vinylidene-bisphosphonic acid hydrate (M~200, 4.72 g. ca 24 mmol), 5.09 g of PAA-BP were obtained, with the modification extent of 70%.

EXAMPLE 1b

Thiol-Modified PAABP

Another type of highly reactive group which can be incorporated into the polymeric bisphosphonates is a thiol group, which can be in a latent form to prevent the oxidative cross-linking of the polymers. Polymeric bisphosphonates containing latent thiol groups can be prepared from PAABP and succinimidyl 3-propyldithiopropionate, according to the reaction sequence shown in FIG. 9c.

Succinimidyl 3-propyldithiopropionate is characterized by $^1$H NMR (CDCl$_3$, $\delta$, ppm): 1.00 (t, 7 Hz, 3H, CH$_3$), 1.72 (sext., 7 Hz, 2H, CH$_2$ in the middle of propyl chain), 2.69 (t, 7 Hz, 2H, CH$_2$S of propyl chain), 2.85 (br. s, 4H, protons of succinimidyl ring), 2.98 and 3.07 (two symmetrical m, 2H and 2H, CH$_2$CH$_2$CO).

In a manner analogous to the preparation of PAABP, polymers with various levels of modification with both the bisphosphonate and the latent thiol groups can be readily synthesized and characterized by $^1$H and $^{31}$P NMR. Thiol groups immobilized on the metal surface (after reduction of propyldithio groups) can then be quantified by a thiol binding assay using dansyl cysteine (DC) and the fluorescence method described below after transformation of the thiol groups into the thiol-reactive 3-carboxy-4-nitrophenyldithio groups with an excess of Ellman's Reagent.

Figure 9A:
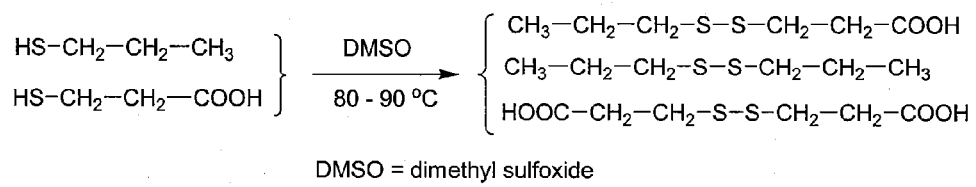
FIGS. 9a, 9b, 9c, and 9d are reactions, and conditions under which they are best performed, in which polybisphosphonates with latent thiol functions are prepared.
Figure 9B:
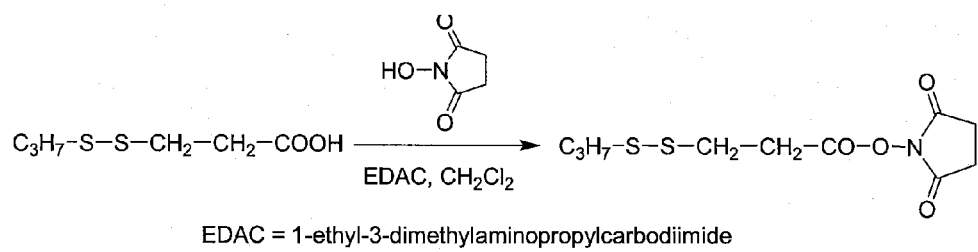
Figure 9C:
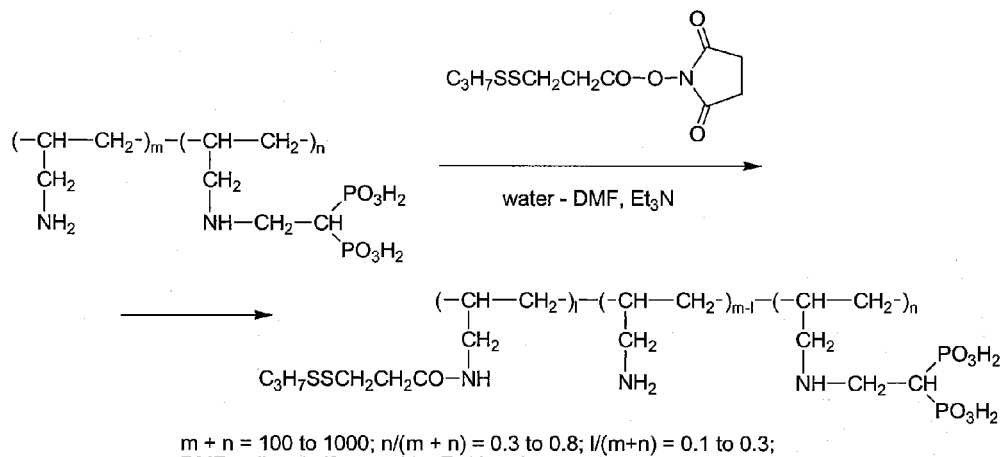
Figure 9D:
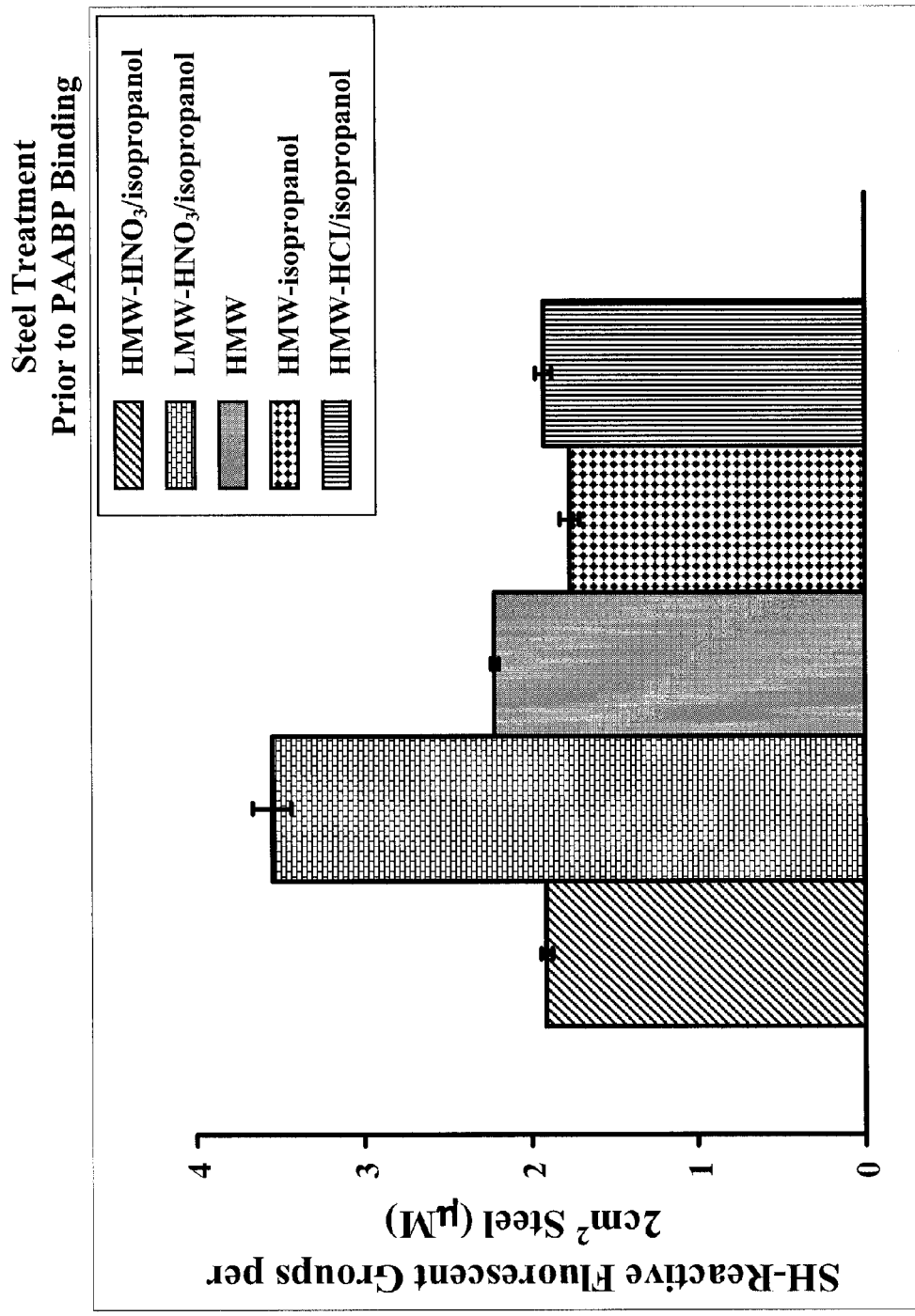

Using the DC fluorescence assay, it was possible to demonstrate that steel surfaces pretreated with a mixture of nitric acid and isopropanol gave rise to the highest density of pyridyldithio groups tethered via low molecular weight (LMW) PAABP to steel surfaces. As shown in FIG. 9d, PAABP prepared from polyallylamine of 15,000 g/mol as described above resulted in the highest —SH group capacity on steel that had been treated with nitric acid and isopropanol. In contrast, other combinations of pretreated or untreated steel and PAABP led to much lower —SH group capacities.

EXAMPLE 2

Coordinative Binding of Anti-Virus Antibody to Tether a Virus Vector on a Stainless Steel Surface Thirty milligrams of polyallylamine (Sigma Aldrich, St. Louis, Mo.) modified with bisphosphonate groups (PAA-BP, 70% bisphosphonate modified) were mixed with 11 mg of potassium bicarbonate and dissolved in 1 ml distilled water by incubating at 60 C to form a 3% (w/v) potassium PAA-BPaqueous solution with pH approximately 5.5. In this example, two polyallylamines of different molecular weights were used in the modifications: one with MW=15 kDa and the other with MW=70 kDa (as determined for the corresponding hydrochlorides using size-exclusion chromatography).

Stainless steel stents were incubated in the potassium PAA-BP solution for 24 hours at 60° C. to bind the polymeric bisphosphonate to the metal surface, then rinsed in distilled water to remove unbound PAA-BP. For further reaction with SPDP crosslinker (Pierce), the stent was equilibrated in pH 7.4 PBS buffer and was incubated for 2 hours at room temperature with a solution of 0.6 mg SPDP in 50 μl dimethyl sulfoxide (DMSO) and 50 μl 1× PBS (pH 7.4) to become "SPDP-activated".

For the purpose of tethering adenovirus to the steel stents, a specific anti-adenovirus knob F(ab')$_2$ antibody fragment was chemically coupled to the SPDP activated steel stent. The chemistry in this experiment involved a reaction between the sulfhydryl groups in the F(ab')$_2$ molecules and the pyridyl disulfide residue of the SPDP molecules. This was done as follows: A stock solution of anti-adenovirus knob F(ab')$_2$ (1.3 μg/μl) was diluted 25 fold in 1× PBS. The SPDP activated stents were incubated in this solution for 5 hours at 37 C. and for overnight at room temperature. The stents were then removed from the solution and rinsed with PBS. The stents were further incubated in bovine serum albumin (BSA, 10 mg/ml in PBS) for 1 hour at 37 C. to eliminate any possible non-specific virus binding. The stents were then rinsed with 1× PBS 5 times (using 20 ml each) and equilibrated with 1× PBS for virus binding.

Rhodamine conjugated secondary antibody was incubated with an anti-adenovirus knob F(ab)'$_2$ antibody bound stent or stainless steel stent without anti-adenovirus knob F(ab)'$_2$ antibody at 37 C. for 1 hour. Efficacy of antibody binding on the stent was verified by using a fluorescence microscope. The stents without bound antibody were also treated in the same way with Rhodamine IgG as control. Stents in both groups were rinsed with PBS and shaken in PBS for two days with frequently changing the washing solution before observed under a fluorescence microscope. Strong Rhodamine fluorescence was observed on only the anti-knob bound stents. The control stent was totally back without any auto-fluorescence under the Texas Red filter. The results further verified that the antibody binding on the stents is very strong and is stable after exhaustive washing.

Pamidronate-modified stainless steel stents were similarly prepared following the general procedure described earlier.

Figure 10:
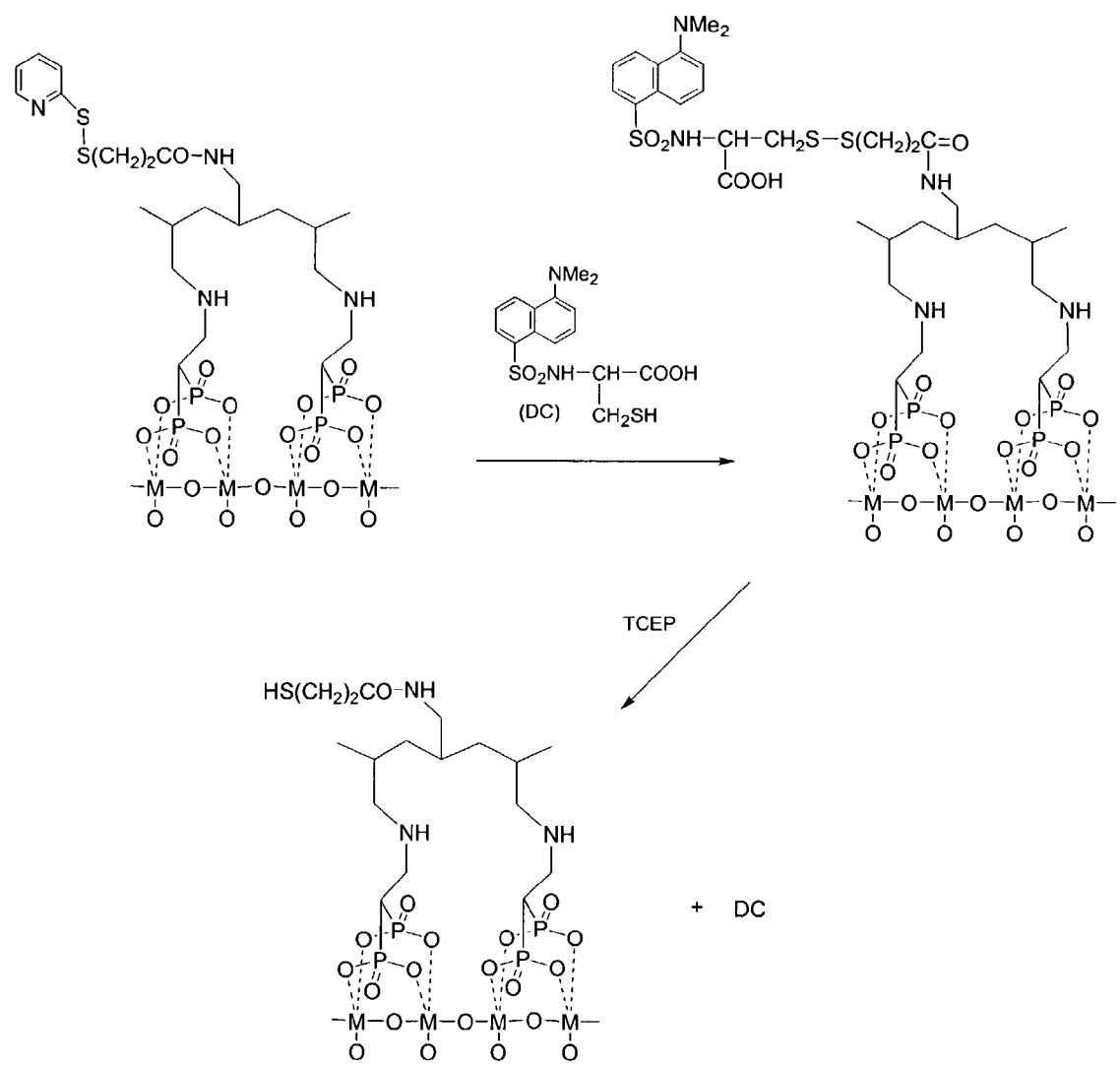
FIG. 10 is a reaction sequence showing how dansyl cysteine (DC) is attached, and reductively removed from, a chemosorbed layer, thereby forming an assay for the number of thiol reactive groups on the chemosorbed layer.
Figure 11A:
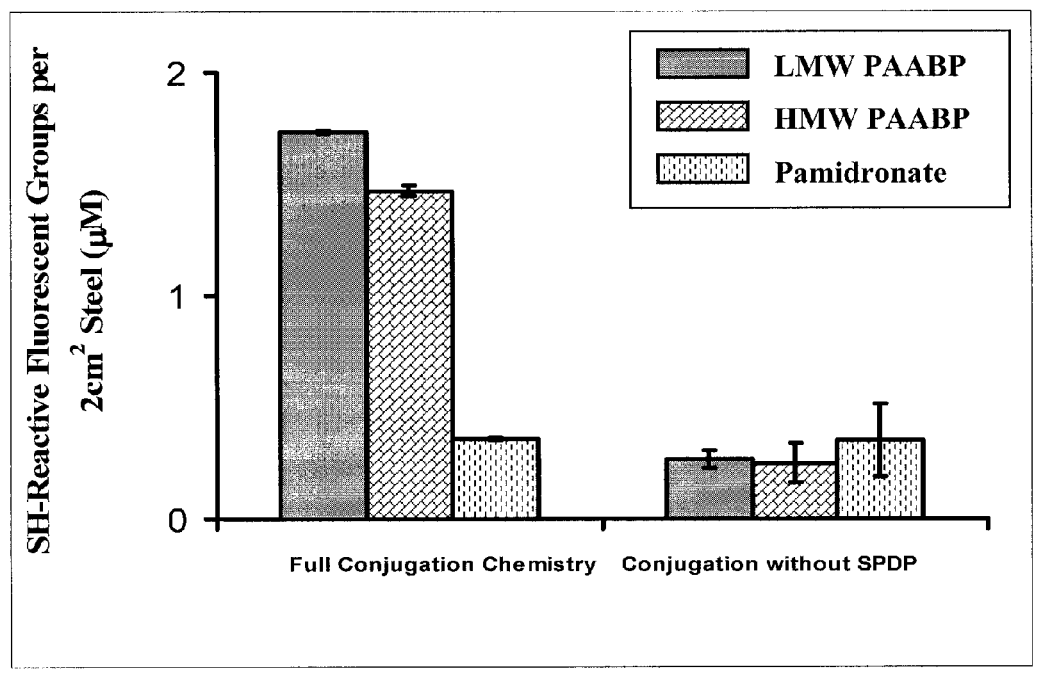
FIGS. 11a and 11b compare the densities of —SH groups on PAABP-modified steel surfaces.

Next, the endpoints in these studies utilized a dansyl cysteine (DC) fluorescent assay to detect thiol-reactive compounds (FIG. 10). The results of these experiments were highly successful, demonstrating that although both pamidronate and PAABP could tightly conjugate to steel, polyallylamine, because of the multi-functionality of this bisphosphonate activated polymer, had significantly higher levels of binding, and also greater potential vector binding capacity (FIG. 11a).

This DC assay was used to assess initial formulation variables of interest concerning PAABP molecular weight effects. The PAABP of higher molecular weight (70 kDa; HMW PAABP) was expected to yield a more stable chemosorption layer (due to the increased number of chelating bisphosphonate groups), whereas the PAABP of lower molecular weight (15 kDa; LMW PAABP) might appear to have a better kinetics of chemosorption (because of easier assembly of the monolayer). However, the low molecular weight PAA resulted in a higher level of sulfhydryl activity (FIG. 11a) and therefore greater vector binding capacity.

EXAMPLE 3

Effect of SPDP Activated PAABP

An adenovirus preparation was fluorescence-labeled with the vector Cy3 (50) using a standard succinimidyl ester approach. Specific red fluorescence was observed when 316L steel modified with tethered virus was exposed to the vector. Red fluorescence was also observed in cells exposed to the modified steel surface, thus demonstrating cell transfection by the tethered Cy3-adenovirus. In contrast, no fluorescence was observed when the labeled vector was exposed to 316L steel surfaces that were treated similarly except for the omission of the SPDP-activation step.

Figure 11B:
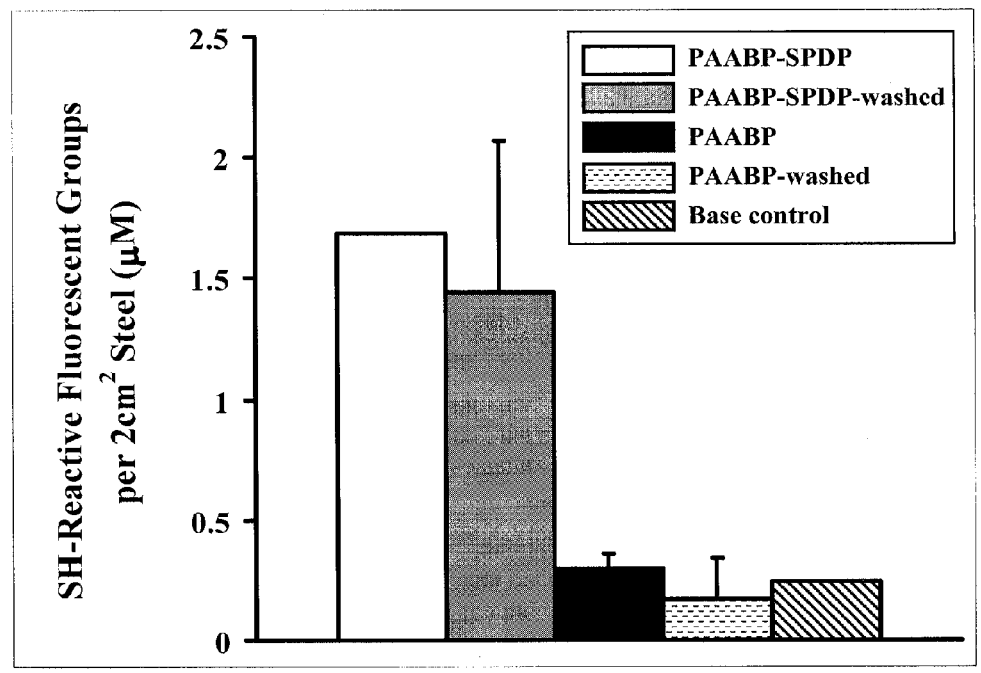

To determine whether a chemosorbed complex will persist in vivo, the stability of the SH-reactive groups and the stability of the coating (after dansylation) were evaluated in a series of one-week pH 7.4 incubations studies. FIG. 11b shows that little loss of SH groups occurs, suggesting that the chemosorbed complex will likely persist in vivo for enabling gene transfer.

EXAMPLE 4

In Vitro Cell Culture Results with Bisphosphonate-Steel Antibody Conjugates

A type 5 adenovirus vector encoding GFP was used in this experiment. Stainless steel stents were incubated with amino-pamidronate, SPDP and anti-adenovirus knob F(ab)'$_2$ antibody; amino-pamidronate and SPDP; amino-pamidronate only; or a stent only, without modification. The specific anti-adenovirus knob F(ab')$_2$ bound stents were incubated in the ad-GFP solution for 1 hour at 37 C. The virus loading in the incubation pool was $1\times10^8$ pfu/stent for all groups. The stents were then removed from the virus pool and rinsed with PBS followed by overnight washing. Images obtained by atomic force microscopy confirmed that high levels of vector immobilization could be achieved by this method.

The virus binding efficacy was evaluated in vitro using rat A10 arterial smooth muscle cells. A cell suspension of $5\times10^4$ A10 cells per ml of M199 medium was prepared with 10% FBS and 1% penicillin/streptomycin. The stent was rinsed with M199 medium once and equilibrated in the M199 medium at 37 C. for 10 minutes in a 6 well culture plate. The medium from the wells was aspirated, holding the stents, and 2 ml cell suspension was added to each well. Cell transduction was observed by fluorescence microscopy using a FITC filter. Strong fluorescence is seen only in stents incubated with amino-pamidronate, SPDP and anti-adenovirus knob F(ab)'$_2$ antibody, indicating that transduction efficiency is markedly improved with the use of antibodies specific for gene vectors. 90% of cells with adenovirus GFP anti-the antibody bound stent were transduced. In contrast, few cells were transduced in the control stents, i.e., those not modified with anti-adenovirus knob F(ab)'$_2$ antibody. Consequently, transduction efficiency is enhanced in vitro in antibody-bound stents compared to control stents. Qualitatively greater amounts of GFP expression were observed via fluorescence with PAABP-modified stents.

Furthermore, a highly sensitive adenovirus detection assay was established using 293 cell cultures, which have adenovirus packaging capability for the replication defective adenovirus used in these studies. The replication defective adenovirus constructs lack the E1&E3 elements, and were inserted into 293 cells, thereby conferring packaging capability. Thus, GFP fluorescence with vector delivery in 293 cultures was amplified due to the ability of the 293 cells to permit vector synthesis at a high level prior to cell death. Steel surfaces which were modified with a PAABP-albumin linkage (control) gave rise to no fluorescence. Further, little fluorescence was observed with the antibody, but strong fluorescence resulted from immobilized reduced antibody, thus demonstrating the specificity of tethering, and the importance of Ab reduction.

Additionally, the utility of using protein A to increase IgG binding was evaluated for its effect on enhancing vector tethering. The results of these studies indicate that PAABP-SPDP-antivector IgG with reduced antibody is superior to protein A, a well known IgG binding protein. This plaque assay result translates to $10^8$ viral particles/cm$^2$ for the tested formulation with the highest vector binding.

EXAMPLE 5

Virus Tethering to Stainless Steel and in Vivo Cell Transduction

A type 5 adenovirus vector encoding GFP was used in this experiment. Anti-adenovirus knob F(ab)'$_2$ antibody bound stents were incubated with and without adenovirus GFP. Stents were implanted in a pig artery. The virus loading in the incubation pool was $1\times10^{10}$ pfu/stent for pig implantation.

Intense neointimal expression of GFP was documented after one week in stents with adenovirus GFP, but not in control artery. Fluorescent photomicrographs indicate the feasibility of this approach for actual blood stream, stent-based delivery of an adenovirus tethered via coordination chemistry.

EXAMPLE 6

Optimizing Cell Transduction when using a Metal Support

Pamidronate binding on a stent surface was evaluated for surface phosphate content by scanning electron microscopy (SEM) and energy dispersive X-ray spectroscopy (EDAX). The results are shown in Table 1. Phosphate content was related to the conditions of the binding reaction.

TABLE 1

Formulation of potassium pamidronate coating on steel stent

| Description/Group | 2M-7A | 2M-7B | 4M-7 | 8M-7 | 2M-5 | 4M-5A | 4M-5B | 8M-5 |
|---|---|---|---|---|---|---|---|---|
| Pamidronic acid (mg) | 235 | 235 | 470 | 940 | 235 | 470 | 470 | 940 |
| $KHCO_3$ (mg) | 200 | 200 | 400 | 800 | 100 | 200 | 200 | 400 |
| Treated time (h) | 24 | 5 | 5 | 5 | 24 | 24 | 5 | 24 |
| Treated temperature (C.) | 37 | 37 | 37 | 37 | 37 | 37 | 37 | 37 |
| Water (mL) | 0.5 | 0.5 | 0.5 | 0.5 | 0.5 | 0.5 | 0.5 | 0.5 |
| Final pH | 7 | 7 | 7 | 7 | 5 | 5 | 5 | 5 |
| Final molar concentration (M) | 1.61 | 1.61 | 2.70 | 4.08 | 1.79 | 3.23 | 3.23 | 5.41 |
| Phosphorus content on stent surface (relative to Fe) (%) | not detectable | not detectable | not detectable | 0.5 | 10 | 30 | 0.5 | 50 |

A10 smooth muscle cells were transduced with SPDP-anti-adenovirus knob F(ab)'$_2$ antibody-adenovirus GFP bound stainless steel rods, and pretreated with either 1.5 M pamidronate, 3.0 M pamidronate or 5.0 M pamidronate. Cell transduction was proportional to the pamidronate concentration used in a reaction. Flat stainless steel rods (the pre-form of a stent) treated with 1.5 M pamidronate showed much less cell transduction than the one treated with 3.0 M pamidronate. Stents treated with 5 M pamidronate did not show much increase in cell transduction, indicating that the 3 M concentration of pamidronate is optimal. Accordingly, A10 cell transduction efficiency is related to pamidronate concentration used in the reaction.

Figure 12A:
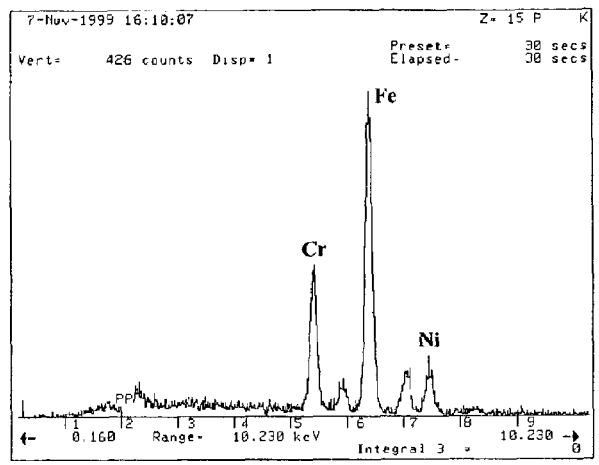
FIGS. 12a 12b and 12c show elemental spectra on EDAX of stainless steel rods.
Figure 12B:
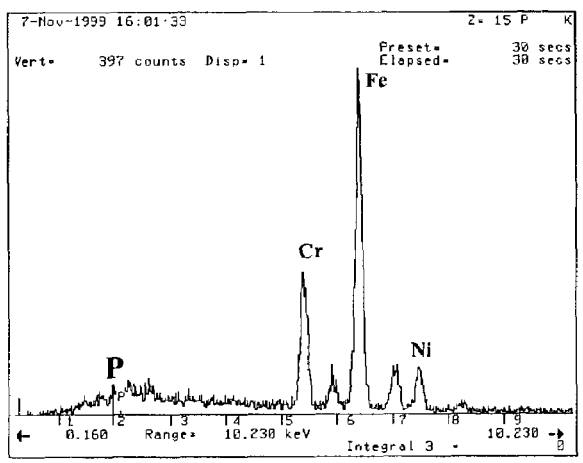
Figure 12C:
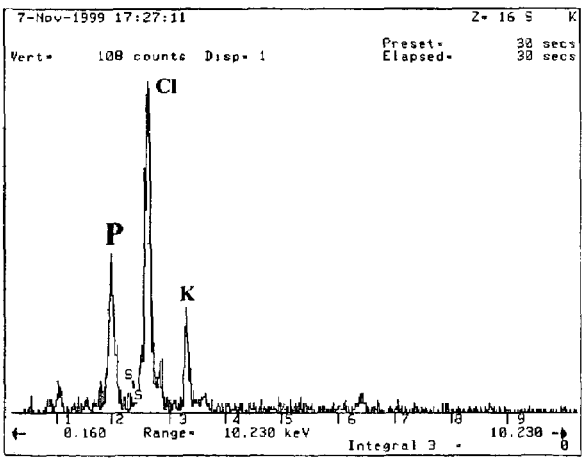

Furthermore, elemental spectra on EDAX from the SEM results (from Table 1) are shown in FIGS. 12a, 12b, and 12c. Elemental spectra of stainless steel rods were determined for baseline (FIG. 12a), after reaction with pamidronate at pH 7.0 (FIG. 12), and after reaction with pamidronate at pH 5.0 (FIG. 12c). At pH 5, the phosphorus signal is maximized and the metal signals are not seen, indicating complete surface coverage with amino-bisphosphonate at this condition. The proportion of metal signals is related to pH of the pamidronate reaction.

EXAMPLE 7

Preparation of Polybisphosphonate Containing Propyldithio Groups as Latent Thiol Functions 3-Propyldithiopropionic acid was prepared by cross-oxidation of propanethiol in the presence of 3-mercaptopropionic acid with DMSO at 80-90° C., and the target compound was separated from the two symmetrical disulfides by vacuum-distillation at 0.1 mm Hg, Bp. 100-103° C. (FIG. 9a).

3-Propyldithiopropionic acid was transformed into its N-hydroxysuccinimide ester (FIG. 9b) as follows: 3-Propyldithiopropionic acid (3.61 g, 20 mmol) and N-hydroxysuccinimide (2.49 g, 21 mmol) were dissolved in $CH_2Cl_2$ (130 ml), and 1-ethyl-3-dimethylaminopropylcarbodiimide hydrochloride (5.00 g, 26 mmol) was added. The mixture was stirred at 20-22° C. overnight and dried in vacuo. Toluene (100 ml) was added to the residue, and the organic phase was washed in sequence with 5% aq. $NaH_2PO_4$ (2×100 ml), with 5% aq. $KHCO_3$ (100 ml) and with saturated aq. $Na_2SO_4$ (75 ml). After drying over $Na_2SO_4$ and removal of the solvent in vacuo, the residue (6.17 g) was dissolved in a mixture of toluene (100 ml) and ethyl acetate (25 ml) and filtered through a pad of silica gel (d=2 cm, l=10 cm), the sorbent was washed with a mixture of toluene and ethyl acetate (4:1, 125 ml). The filtrate was dried in vacuo to leave a crystalline residue of the aim N-hydroxysuccinimide ester, yield 5.23 g (94%). $^1$H NMR ($CDCl_3$), δ, ppm: 1.00 (t, 7 Hz, $CH_3$), 1.72 (sext., 7 Hz, $CH_2$ in the middle of propyl radical), 2.69 (t, 7 Hz, $CH_2SS$ of propyl radical), 2.85 (br. s, protons of succinimidyl group), 2.98 and 3.07 (two symmetrical m, $CH_2CH_2CO$).

Polyallylamine modified with ca. 70% of 2,2-diphosphonoethyl groups as described in Example 1b (2.00 g, containing approximately 7.5 mmol of bisphosphonate groups and ca. 3 mmol of intact primary amino groups) was dissolved in a mixture of water (7.4 ml) and triethylamine (1.55 ml, 11.1 mmol). The viscous homogeneous solution was diluted with DMF (14 ml), and N-hydroxysuccinimide ester of 3-propyldithiopropionic acid (0.99 g, 3.57 mmol) was added as a solution in DMF (7 ml). The reaction mixture was stirred at 20-22° C. for 2 h, then more triethylamine (0.10 ml, 0.7 mmol) was added, and the second portion of 3-propyldithiopropionic acid N-hydroxysuccinimide ester (0.20 g, 0.7 mmol) was introduced in DMF (0.5 ml). The mixture was stirred at 20-22° C. for 3 days, diluted with water (39 ml) and filtered. The filtrate was acidified with $CF_3COOH$ (6.0 ml, 78 mmol), the resulting suspension was diluted with methanol (80 ml), and the precipitate of polymer was filtered off. After washing in sequence with methanol (100 ml), with a mixture of methanol and $CF_3COOH$ (50:1, 80 ml), with methanol (80 ml), with 2-propanol (40 ml) and with pentane (25 ml), the polymer was air dried to the constant weight 2.03 g. According to 1H NMR analysis, the extent of modification with 3-propyldithiopropionyl groups in the manner depicted in FIG. 9c was found to be 10% (l/m+n=0.1). The extent of modification was calculated from the intensities of bands at δ=1.0 ppm ($CH_3$) and δ=1.7 ppm ($CH_2$ in the middle of propyl chain).

EXAMPLE 8

Affinity Pairing for Gene Vector Attachment

Gene vectors may attached to metal surfaces using a variety of affinity pairing systems. This example demonstrates the use of avidin-biotin affinity.

Replication defective adenoviruses can be biotinylated with complete retention of functionality according to the procedures of Smith et al. (*PNAS*, 96, 8855-8860, 1999) which is incorporated herein by reference in its entirety. Metal surface modification by polyaminobisphosphonate or polybisphosphonate with latent thiol functions with or without amplification can be carried out as illustrated above.

Figure 13:
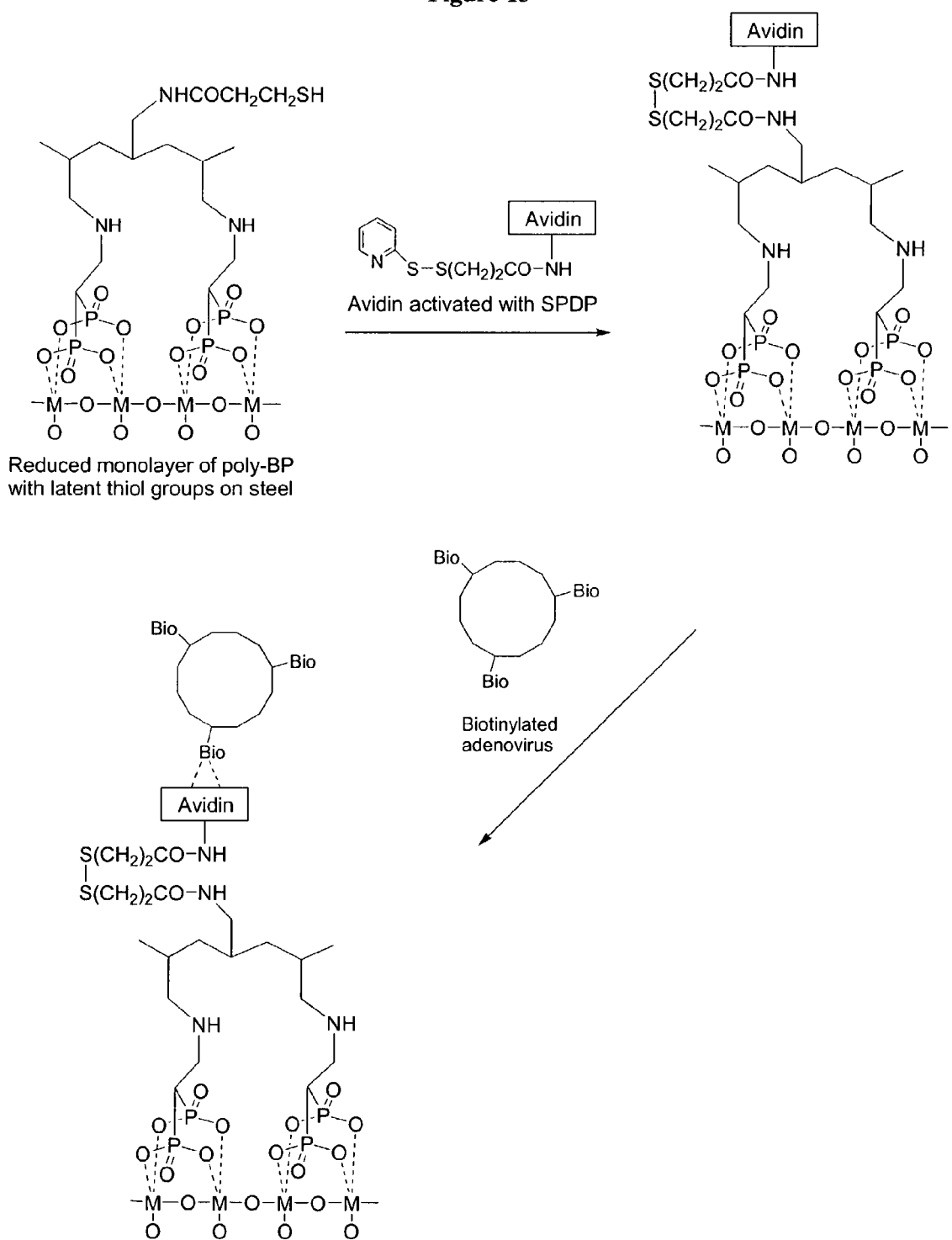
FIG. 13 depicts a reaction sequence showing the use of an avidin-modified steel surface to bind a biotinylated adenovirus.

As exemplified by the reaction sequence in FIG. 13, avidin can be directly attached to the reactive functionalities of the surface-modified metal. Alternatively, avidin may be indirectly bound to a metal surface through a biotin linkage, where biotinylated avidin is used as a starting material. In either of these embodiments, the surface-bound avidin can readily bind biotinylated adenoviruses, which can be processed by arterial smooth muscle cells interacting with the metal surface, thereby leading to successful transduction.

Following the procedure outlined above for the second embodiment, metal surface-bound PAABP was modified with biotinylated avidin. The addition of a fluorescently labeled biotinylated adenovirus (bioAdV) gave rise to strong fluorescence, thus demonstrating the specific binding of bioAdV to the surface-bound avidin. In analogous experiments where either the adenovirus was not biotinylated or avidin was not linked to the surface-bound PAABP, no fluorescence was observed. These results show that the biotin-avidin linkage is required.

It will be apparent to those skilled in the art that various modifications and variations can be made in the methods and compositions of the present invention without departing from the spirit or scope of the invention. Thus, it is intended that the present invention cover such modifications and variations as circumscribed by the appended claims and their equivalents.

We claim:

1. A composition comprising a surface modifier, a biologically active molecule covalently attached to said surface modifier directly or via a crosslinker, and a medical device having a metal surface to which said surface modifier is chemically coordinated, wherein said surface modifier is a functionalized bisphosphonate depicted by a formula

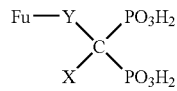

wherein X is H, an alkyl, or OH, Fu is $NH_2$, SH, a maleimido group, a vinylsulfonyl group, an epoxy group or an iodoacetamido group, and Y is a polyamine.

2. The composition of claim 1, wherein the biologically active molecule is attached to the surface modifier via a crosslinker.

3. The composition of claim 2 wherein said crosslinker is selected from the group consisting of HBVS, EMCS, BMH, DPDPB and SPDP.

4. The composition of claim 3, wherein said crosslinker is SPDP.

5. The composition of claim 1, wherein said biologically active molecule is one component of an affinity-ligand pair.

6. The composition of claim 5, wherein said component is one selected from the group consisting of an antibody, avidin, biotin, protein A, transferrin, and a receptor for transferrin.

7. The composition of claim 6, wherein said component is an antibody.

8. The composition of claim 7, wherein said antibody is a thiol-modified antibody.

9. The composition of claim 7, wherein said antibody is selected from the group consisting of a full-length antibody, an Fc antibody fragment, an Fab' antibody fragment, an F(ab')2 antibody fragment and a single chain antibody.

10. The composition of claim 9, wherein said antibody is a full-length antibody.

11. The composition of claim 9, wherein said antibody is an F(ab')2 antibody fragment.

12. The composition of claim 7, further comprising a nucleic acid to which said antibody specifically binds.

13. The composition of claim 12, wherein said nucleic acid is DNA or RNA.

14. The composition of claim 13, wherein said nucleic acid is DNA.

15. The composition of claim 12, wherein said nucleic acid comprises a vector system.

16. The composition of claim 15 wherein said vector system is selected from the group consisting of a plasmid, adenovirus, retrovirus, adeno-associated virus, and herpes simplex virus.

17. The composition of claim 16 wherein said vector system is an adenovirus.

18. The composition of claim 1, wherein said surface comprises a stainless steel surface.

19. A method of making a therapeutic delivery system comprising the composition of claim 1, the method comprising the steps of
    providing the medical device having the metal surface;
    providing the surface modifier;
    providing the biologically active molecule;
    optionally providing a crosslinker;
    contacting the metal surface with the surface modifier to make a modified surface; and
    contacting the modified surface with the biologically active molecule and optionally with the crosslinker, thereby making the therapeutic delivery system.

20. The method of claim 19, wherein said biologically active molecule is one component of an affinity ligand pair.

21. The method of claim 20, wherein said component is one selected from the group consisting of an antibody, avidin, biotin, protein A, transferrin, and a receptor for transferrin.

22. The method of claim 21, wherein said component is an antibody.

23. The method of claim 22, wherein said antibody is selected from the group consisting of a full-length antibody, an Fc antibody fragment, an Fab' antibody fragment, an F(ab')2 antibody fragment and a single chain antibody.

24. The method of claim 23, wherein said antibody is a full-length antibody.

25. The method of claim 23, wherein said antibody is an F(ab')2 antibody fragment.

26. The method of claim 21, further comprising a nucleic acid to which said antibody specifically binds.

27. The method of claim 26, wherein said nucleic acid is DNA or RNA.

28. The method of claim 27, wherein said nucleic acid is DNA.

29. The method of claim 26, wherein said nucleic acid comprises a vector system.

30. The method of claim 29 wherein said vector system is selected from the group consisting of a plasmid, adenovirus, retrovirus, adeno-associated virus, and herpes simplex virus.

31. The method of claim 29 wherein said vector system is an adenovirus.

32. The method of claim 19, wherein said surface comprises a stainless steel surface.

33. A method for delivering a biologically active molecule, the method comprising exposing a cell to the composition of claim 1 having the biologically active molecule covalently bound to said surface modifier directly or via a crosslinker.

34. The method of claim 33, wherein said surface modifier is a polyaminobisphosphonate.

35. The method of claim 33, wherein said biologically active molecule is one component of an affinity ligand pair.

36. The method of claim 35, wherein said component is one selected from the group consisting of an antibody, avidin, biotin, protein A, transferrin, and a receptor for transferrin.

37. The method of claim 36, wherein said component is an antibody.

38. The method of claim 37, wherein said antibody is a thiol modified antibody.

39. The method of claim 37, wherein said antibody is selected from the group consisting of a full-length antibody, an Fc antibody fragment, an Fab' antibody fragment, an F(ab')2 antibody fragment and a single chain antibody.

40. The method of claim 39, wherein said antibody is a full-length antibody.

41. The method of claim 39, wherein said antibody is an F(ab')2 antibody fragment.

42. The method of claim 37, further comprising a nucleic acid to which said antibody specifically binds.

43. The method of claim 42, wherein said nucleic acid is DNA or RNA.

44. The method of claim 43, wherein said nucleic acid is DNA.

45. The method of claim 42, wherein said nucleic acid comprises a vector system.

46. The method of claim 45, wherein said vector system is selected from the group consisting of a plasmid, adenovirus, retrovirus, adeno-associated virus, and herpes simplex virus.

47. The method of claim 46 wherein said vector system is an adenovirus.

48. The method of claim 33, wherein said surface comprises a stainless steel surface.

49. The method of claim 33, wherein the surface modifier is depicted by a formula

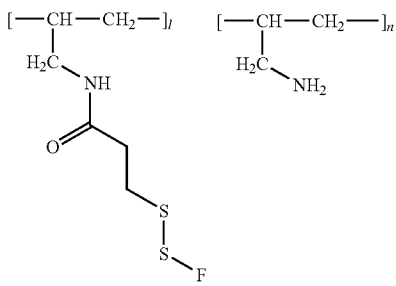

-continued

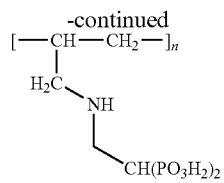

wherein F is propyl or 2-pyridyl; m and n are integers ≧ zero; l is an integer ≦ m; m+n=100 to 1000; n/(m+n)= 0.3 to 0.8; and l/(m+n)=0.1 to 0.3.

50. The composition of claim 1, wherein SH is a latent SH group.

51. The composition of claim 1, wherein the polyamine is depicted by a formula

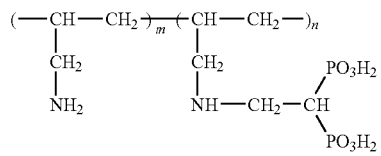

wherein m+n=100 to 1000 and n/(m+n)=0.3 to 0.8.

52. The composition of claim 1, wherein the surface modifier is a polyaminobisphosphonate.

53. The composition of claim 1, wherein the polyamine is a polyallylamine.

54. The composition of claim 1, wherein the polyamine is polylysine.

55. A composition comprising a surface modifier, a biologically active molecule covalently attached to said surface modifier directly or via a crosslinker, and a medical device having a metal surface to which said surface modifier is chemically coordinated, wherein the surface modifier is depicted by a formula

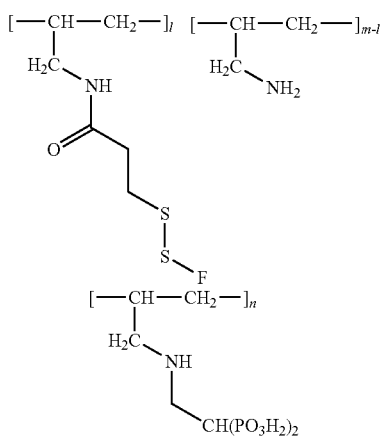

wherein F is propyl or 2-pyridyl; m and n are integers ≧ zero; l is an integer ≦ m; m+n=100 to 1000; n/(m+n)= 0.3 to 0.8; and l/(m+n)=0.1 to 0.3.

* * * * *

UNITED STATES PATENT AND TRADEMARK OFFICE
CERTIFICATE OF CORRECTION

PATENT NO. : 7,589,070 B2  Page 1 of 1
APPLICATION NO. : 10/170411
DATED : September 15, 2009
INVENTOR(S) : Levy et al.

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 308 days Delete the phrase "by 308 days" and insert -- by 796 days --

Signed and Sealed this

Thirty-first Day of August, 2010

David J. Kappos
*Director of the United States Patent and Trademark Office*